(12) United States Patent
Maltais et al.

(10) Patent No.: US 7,456,190 B2
(45) Date of Patent: *Nov. 25, 2008

(54) COMPOSITIONS USEFUL AS PROTEIN KINASE INHIBITORS

(75) Inventors: Francois Maltais, Tewksbury, MA (US); Alex Aronov, Watertown, MA (US); Michael R. Hale, Bedford, MA (US); Young-Choon Moon, Belle Meade, NJ (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 625 days.

This patent is subject to a terminal disclaimer.

(21) Appl. No.: 10/798,766

(22) Filed: Mar. 11, 2004

(65) Prior Publication Data

US 2004/0220200 A1   Nov. 4, 2004

Related U.S. Application Data

(60) Provisional application No. 60/454,405, filed on Mar. 13, 2003.

(51) Int. Cl.
*A61K 31/506* (2006.01)
*A61K 31/4439* (2006.01)
*A61K 31/401* (2006.01)
*C07D 403/04* (2006.01)
*C07D 401/14* (2006.01)
*C07D 207/34* (2006.01)

(52) U.S. Cl. .................. 514/275; 514/343; 514/422; 544/324; 546/279.1; 548/518

(58) Field of Classification Search .............. 548/518; 514/275, 343, 422; 544/324; 546/279.1
See application file for complete search history.

(56) References Cited

U.S. PATENT DOCUMENTS 6,743,791 B2 *  6/2004  Cao et al. ............... 514/235.8
2004/0229875 A1 * 11/2004  Cao et al. ................ 514/242
2006/0106069 A1 *  5/2006  Martinez-Botella et al. . 514/343

FOREIGN PATENT DOCUMENTS

WO    WO 02064586 A2 *  8/2002

OTHER PUBLICATIONS

Patani et al. "Bioisosterism: A Rational Approach in Drug Design" Chemical Reviews 1996, vol. 96, pp. 3147-3176.*
Patani et al. "Bioisosterism: A Rational Approach in Drug Design" Chemical Reviews, 1996, vol. 96, pp. 3147-3176.*
Brownlees, et al., "Tau Phosphorylation in Transgenic Mice Expressing Glycogen Synthase Kinase-3β Transgene", *NeuroReport*, 8: 3251-3255, 1997.
Carmichael, et al., "Glycogen Synthase Kinase-3β Inhibitors Prevent Cellular Polyglutamine Toxicity Caused by the Huntington's Disease Mutation", *The Journal of Biological Chemistry*, 277(37): 33791-33798, 2002.
Cohen, et al., "The Renaissance of GSK3", *Molecular Cell Biology*, 2:769-776, 2001.
Cohen, et al., "Dissection of the Protein Phosphorylation Cascades Involved in Insulin and Growth Factor Action", *Twenty-Fourth Ciba Medal Lecture*, 21: 555-567, 1993.
Cross, et al., "The Inhibition of Glycogen Synthase Kinase-3 by Insulin or Insulin-Like Growth Factor 1 in the Rat Skeletal Muscle Cell Line L6 is Blocked by Wortmannin, But Not by Rapamycin: Evidence that Wortmannin Blocks Activation of the Mitogen-Activated Protein Kinase Pathway in L6 Cells Between Ras and Raf", *Biochem. J.* 303: 21-26, 1994.
Fabbro, et al., Protein Kinases as Targets for Anticancer Agents: From Inhibitors to Useful Drugs', *Pharmacology & Therapeutics*, 93: 79-98, 2002.
Kaytor, et al., "The GSK3β Signaling Cascade and Neurodegenerative Disease", *Current Opinion in Neurobiology*, 12: 275-278, 2002.
Klein, et al., "A Molecular Mechanism for the Effect of Lithium on Development", *Proc. Natl. Acad. Sci. USA*, 93: 8455-8459, 1996.
Massillon, et al., "Identification of the Glycogenic Compound 5-Iodotubercidin as a General Protein Kinase Inhibitor", *Biochem J.* 299: 123-128, 1994.
Phiel, et al., "GSK-3α Regulates Production of Alzheimer's Disease Amyloidβ Peptides", *Nature*, 423: 435-439, 2003.
International Search Report issued for corresponding PCT application PCT/US2004/007540.

* cited by examiner

*Primary Examiner*—Golam M. M. Shameem
*Assistant Examiner*—Joseph R Kosack
(74) *Attorney, Agent, or Firm*—Daniel A. Pearson

(57) ABSTRACT

The present invention relates to compounds useful of inhibitors of protein kinases. The invention also provides pharmaceutically acceptable compositions comprising said compounds and methods of using the compositions in the treatment of various disease, conditions, or disorders.

9 Claims, No Drawings

COMPOSITIONS USEFUL AS PROTEIN KINASE INHIBITORS

CROSS REFERENCE TO RELATED APPLICATIONS

This application claims priority to U.S. Provisional Patent Application Ser. No. 60/454,405, filed Mar. 13, 2003 the contents of which are incorporated herein by reference.

TECHNICAL FIELD OF THE INVENTION

The present invention relates to compounds useful as inhibitors of protein kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II,* Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors useful as therapeutic agents.

ERK Kinase

ERK2 is a widely distributed protein kinase that achieves maximum activity when both Thr183 and Tyr185 are phosphorylated by the upstream MAP kinase kinase, MEK1 (Anderson et al., 1990, Nature 343, 651; Crews et al., 1992, Science 258, 478). Upon activation, ERK2 phosphorylates many regulatory proteins, including the protein kinases Rsk90 (Bjorbaek et al., 1995, J. Biol. Chem. 270, 18848) and MAPKAP2 (Rouse et al., 1994, Cell 78, 1027), and transcription factors such as ATF2 (Raingeaud et al., 1996, Mol. Cell Biol. 16, 1247), Elk-1 (Raingeaud et al. 1996), c-Fos (Chen et al., 1993 Proc. Natl. Acad. Sci. USA 90, 10952), and c-Myc (Oliver et al., 1995, Proc. Soc. Exp. Biol. Med. 210, 162). ERK2 is also a downstream target of the Ras/Raf dependent pathways (Moodie et al., 1993, Science 260, 1658) and relays the signals from these potentially oncogenic proteins. ERK2 has been shown to play a role in the negative growth control of breast cancer cells (Frey and Mulder, 1997, Cancer Res. 57, 628) and hyperexpression of ERK2 in human breast cancer has been reported (Sivaraman et al., 1997, J Clin. Invest. 99, 1478). Activated ERK2 has also been implicated in the proliferation of endothelin-stimulated airway smooth muscle cells, suggesting a role for this kinase in asthma (Whelchel et al., 1997, Am. J. Respir. Cell Mol. Biol. 16, 589).

Overexpression of receptor tyrosine kinases such as EGFR and ErbB2 (Arteaga CL, 2002, Semin Oncol. 29, 3-9; Eccles SA, 2001, J Mammary Gland Biol Neoplasia 6:393-406; Mendelsohn J & Baselga J, 2000, Oncogene 19, 6550-65), as well as activating mutations in the Ras GTPase proteins (Nottage M & Siu L L, 2002, Curr Pharm Des 8, 2231-42; Adjei A A, 2001, J Natl Cancer Inst 93, 1062-74) or B-Raf mutants (Davies H. et al., 2002, Nature 417, 949-54; Brose et al., 2002, Cancer Res 62, 6997-7000) are major contributors to human cancer. These genetic alterations are correlated with poor clinical prognosis and result in activation of the Raf-1/2/3-MEK1/2-ERK1/2 signal transduction cascade in a broad panel of human tumors. Activated ERK (i.e. ERK1 and/or ERK2) is a central signaling molecule that is associated with the control of proliferation, differentiation, anchorage-independent cell survival, and angiogenesis, contributing to a number of processes that are important for the formation and progression of malignant tumors. These data show that an ERK1/2 inhibitor will exert pleiotropic activity, including proapoptotic, anti-proliferative, anti-metastatic and anti-angiogenic effects, and will offer a therapeutic opportunity against a very broad panel of human tumors.

There is a growing body of evidence that implicates constitutive activation of the ERK MAPK pathway in the oncogenic behavior of select cancers. Activating mutations of Ras are found in ~30% of all cancers, with some, such as pancreatic (90%) and colon (50%) cancer, harboring particularly high mutation rates. Ras mutations have also been identified in 9-15% of melanomas, but B-Raf somatic missense mutations conferring constitutive activation are more frequent and are found in 60-66% malignant melanomas. Activating mutations of Ras, Raf and MEK are able to oncogenically transform fibroblasts in vitro, and Ras or Raf mutations in conjunction with the loss of a tumor suppressor gene (e.g. p16INK4A) can cause spontaneous tumor development in vivo. Increased ERK activity has been demonstrated in these models and has also been widely reported in appropriate human tumors. In melanoma, high basal ERK activity resulting from either B-Raf or N-Ras mutations or autocrine growth factor activation is well documented and is associated with rapid tumor growth, increased cell survival and resistance to apoptosis. Additionally, ERK activation is considered a major driving force behind the highly metastatic behavior of melanoma associated with increased expression of both extracellular matrix degrading proteases and invasion-promoting integrins as well as the downregulation of E-cadherin adhesion molecules that normally mediate keratinocyte interactions to control melanocyte growth. These data taken together, indicate ERK as a promising therapeutic target for the treatment of melanoma, a currently untreatable disease.

Aurora Kinase

The Aurora family of serine/threonine kinases is essential for cell proliferation [Bischoff, J. R. & Plowman, G. D. (The Aurora/Ipl1p kinase family: regulators of chromosome segregation and cytokinesis) *Trends in Cell Biology* 9, 454-459 (1999); Giet, R. and Prigent, C. (Aurora/Ipl1p-related kinases, a new oncogenic family of mitotic serine-threonine kinases) *Journal of Cell Science* 112, 3591-3601 (1999); Nigg, E. A. (Mitotic kinases as regulators of cell division and its checkpoints) Nat. Rev. *Mol. Cell Biol.* 2, 21-32 (2001); Adams, R. R, Carmena, M., and Earnshaw, W. C. (Chromosomal passengers and the (aurora) ABCs of mitosis) *Trends in Cell Biology* 11, 49-54 (2001)]. Inhibitors of the Aurora kinase family therefore have the potential to block growth of all tumour types.

Elevated levels of all Aurora family members are observed in a wide variety of tumour cell lines. Aurora kinases are over-expressed in many human tumors and this is reported to be associated with chromosomal instability in mammary tumors (Miyoshi et al 92: 370, 2001).

The three known mammalian family members, Aurora-A ("1"), B ("2") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. In mammalian cells proposed substrates for Aurora include histone H3, a protein involved in chromosome condensation, and CENP-A, myosin II regulatory light chain, protein phosphatase 1, TPX2, all of which are required for cell division.

Since its discovery in 1997 the mammalian Aurora kinase family has been closely linked to tumorigenesis. The most compelling evidence for this is that over-expression of Aurora-A transforms rodent fibroblasts (Bischoff, J. R., et al. A homologue of *Drosophila aurora* kinase is oncogenic and amplified in human colorectal cancers. *EMBO J.* 17: 3052, 1998). Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the aurora-A locus and chromosomal instability in mammary and gastric tumours has been observed. (Miyoshi, Y., Iwao, K., Egawa, C., and Noguchi, S. Association of centrosomal kinase STK15/BTAK mRNA expression with chromosomal instability in human breast cancers. *Int. J. Cancer* 92, 370-373 (2001). (Sakakura, C. et al. Tumor-amplified kinase BTAK is amplified and overexpressed in gastric cancers with possible involvement in aneuploid formation. *British Journal of Cancer* 84: 824 2001).

The Aurora kinases have been reported to be over-expressed in a wide range of human tumours. Elevated expression of Aurora-A has been detected in over 50% of colorectal (Bischoff, J. R., et al. A homologue of *Drosophila aurora* kinase is oncogenic and amplified in human colorectal cancers. *EMBO J.* 17: 3052, 1998) (Takahashi, T., et al. Centrosomal kinases, HsAIRk1 and HsAIRK3, are overexpressed in primary colorectal cancers. *Jpn. J. Cancer Res.* 91: 1007, 2000), ovarian (Gritsko, T. M. et al. Activation and overexpression of centrosome kinase BTAK/Aurora-A in human ovarian cancer. *Clinical Cancer Research* 9: 1420, 2003), and gastric tumors (Sakakura, C. et al. Tumor-amplified kinase BTAK is amplified and overexpressed in gastric cancers with possible involvement in aneuploid formation. *British Journal of Cancer* 84: 824, 2001), and in 94% of invasive duct adenocarcinomas of the breast (Tanaka, T., et al. Centrosomal kinase AIK1 is overexpressed in invasive ductal carcinoma of the breast. *Cancer Research.* 59: 2041, 1999). Furthermore, high levels of Aurora-A have also been reported in renal, cervical, neuroblastoma, melanoma, lymphoma, pancreatic and prostate tumour cell lines. (Bischoff, J. R., et al. A homologue of *Drosophila aurora* kinase is oncogenic and amplified in human colorectal cancers. *EMBO J.* 17: 3052, 1998) (Kimura, M., Matsuda, Y., Yoshioka, T., and Okano, Y. Cell cycle-dependent expression and centrosomal localization of a third human Aurora/Ipl1-related protein kinase, AIK3. *Journal of Biological Chemistry* 274: 7334, 1999)(Zhou et al. Tumour amplifiec kinase STK15/BTAK induces centrosome amplification, aneuploidy and transformation *Nature Genetics* 20: 189, 1998)(Li et al. Overexpression of oncogenic STK15/BTAK/Aurora-A kinase in human pancreatic cancer *Clin Cancer Res.* 9(3): 991, 2003).

Amplification/overexpression of Aurora-A is observed in human bladder cancers and amplification of Aurora-A is associated with aneuploidy and aggressive clinical behaviour (Sen S. et al Amplification/overexpression of a mitotic kinase gene in human bladder cancer *J Natl Cancer Inst.* 94(17): 1320, 2002). Moreover, amplification of the aurora-A locus (20q13) correlates with poor prognosis for patients with node-negative breast cancer (Isola, J. J., et al. Genetic aberrations detected by comparative genomic hybridization predict outcome in node-negative breast cancer. *American Journal of Pathology* 147: 905, 1995). Aurora-B is highly expressed in multiple human tumour cell lines, including leukemic cells (Katayama et al. Human AIM-1: cDNA cloning and reduced expression during endomitosis in megakaryocyte-lineage cells. *Gene* 244:1-7). Levels of this enzyme increase as a function of Duke's stage in primary colorectal cancers (Katayama, H. et al. Mitotic kinase expression and colorectal cancer progression. *Journal of the National Cancer Institute* 91: 1160, 1999). Aurora-C, which is normally only found in germ cells, is also over-expressed in a high percentage of primary colorectal cancers and in a variety of tumour cell lines including cervical adenocarinoma and breast carcinoma cells (Kimura, M., Matsuda, Y., Yoshioka, T., and Okano, Y. Cell cycle-dependent expression and centrosomal localization of a third human Aurora/Ipl1-related protein kinase, AIK3. *Journal of Biological Chemistry* 274: 7334, 1999). (Takahashi, T., et al. Centrosomal kinases, HsAIRk1 and HsAIRK3, are overexpressed in primary colorectal cancers. *Jpn. J. Cancer Res.* 91: 1007, 2000).

Based on the known function of the Aurora kinases, inhibition of their activity should disrupt mitosis leading to cell cycle arrest. In vivo, an Aurora inhibitor therefore slows tumor growth and induces regression.

Aurora-2 is highly expressed in multiple human tumor cell lines and levels increase as a function of Duke's stage in primary colorectal cancers (Katayama, H. et al. (Mitotic kinase expression and colorectal cancer progression) *Journal of the National Cancer Institute* 91: 1160, 1999). Aurora-2 plays a role in controlling the accurate segregation of chromosomes during mitosis. Misregulation of the cell cycle can lead to cellular proliferation and other abnormalities. In human colon cancer tissue, the Aurora-2 protein is over expressed (Bischoff et al., *EMBO J.,* 17: 3052, 1998; Schumacher et al., *J. Cell Biol.,* 143: 1635, 1998; Kimura et al., *J. Biol. Chem.,* 272: 13766, 1997). Aurora-2 is over-expressed in the majority of transformed cells. Bischoff et al found high levels of Aurora-2 in 96% of cell lines derived from lung, colon, renal, melanoma and breast tumors (Bischoff, et al *EMBO J.* 17: 3052, 1998). Two extensive studies show elevated Aurora-2 in 54% and 68% (Bishoff, et al *EMBO J.* 17: 3052, 1998)(Takahashi, et al *Jpn J Cancer Res.* 91: 1007, 2000) of colorectal tumours and in 94% of invasive duct adenocarcinomas of the breast (Tanaka, et al 59: 2041, 1999).

Aurora-1 expression is elevated in cell lines derived from tumors of the colon, breast, lung, melanoma, kidney, ovary, pancreas, CNS, gastric tract and leukemias (Tatsuka, et al 58: 4811, 1998).

High levels of Aurora-3 have been detected in several tumour cell lines, although it is restricted to testis in normal tissues (Kimura, et al 274: 7334, 1999). Over-expression of Aurora-3 in a high percentage (c. 50%) of colorectal cancers has also been documented (Takahashi, et al *Jpn J Cancer Res.* 91, 1007, 2000). In contrast, the Aurora family is expressed at a low level in the majority of normal tissues, the exceptions being tissues with a high proportion of dividing cells such as the thymus and testis (Bischoff, et al *EMBO J.* 17: 3052, 1998).

For further review of the role Aurora kinases play in proliferative disorders, see Bischoff, J. R. & Plowman, G. D. (The Aurora/Ipl1p kinase family:regulators of chromosome segregation and cytokinesis) *Trends in Cell Biology* 9, 454-459 (1999); Giet, R. and Prigent, C. (Aurora/Ipl1p-related kinases, a new oncogenic family of mitotic serine-threonine kinases) *Journal of Cell Science* 112, 3591-3601 (1999); Nigg, E. A. (Mitotic kinases as regulators of cell division and its checkpoints) Nat. Rev. *Mol. Cell Biol.* 2, 21-32 (2001); Adams, R. R, Carmena, M., and Earnshaw, W. C. (Chromosomal passengers and the (aurora) ABCs of mitosis) *Trends in Cell Biology* 11, 49-54 (2001); and Dutertre, S., Descamps, S., & Prigent, P. (On the role of aurora-A in centrosome function) *Oncogene* 21, 6175-6183 (2002).

Glycogen Synthase Kinase

Glycogen synthase kinase-3 (GSK-3) is a serine/threonine protein kinase comprised of α and β isoforms that are each encoded by distinct genes (Coghlan et al., *Chemistry & Biology,* 7: 793, 2000; Kim and Kimmel, *Curr. Opinion Genetics Dev.,* 10: 508, 2000). GSK-3 has been implicated in various diseases including diabetes, Alzheimer's disease, CNS disorders such as manic depressive disorder and neurodegenerative diseases, and cardiomyocyte hypertrophy (see, e.g., WO 99/65897; WO 00/38675; Kaytor and Orr, *Curr. Opin. Neurobiol.,* 12: 275, 2000; Haq et al., *J. Cell Biol.,* 151: 117, 2000; Eldar-Finkelman, *Trends Mol. Med.,* 8: 126, 2002). These diseases are associated with the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPBα. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake (Klein, et al., *PNAS,* 93: 8455, 1996; Cross et al., *Biochem. J.,* 303: 21, 1994; Cohen, *Biochem. Soc. Trans.,* 21: 555, 1993; and Massillon et al., *Biochem J.* 299: 123, 1994; Cohen and Frame, *Nat. Rev. Mol. Cell. Biol.,* 2: 769, 2001). However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that GSK-3 is overexpressed in patients with type II diabetes [WO 00/38675]. Therapeutic inhibitors of GSK-3 are therefore useful for treating diabetic patients suffering from an impaired response to insulin.

Apoptosis has been implicated in the pathophysiology of ischemic brain damage (Li, et al., 1997; Choi, et al., 1996; Charriaut-Marlangue, et al., 1998; Grahm and Chen, 2001; Murphy, et al., 1999; Nicotera, et al., 1999). Recent publications indicate that activation of GSK-3β may be involved in apoptotic mechanisms (Kaytor and Orr, 2002; Culbert, et al., 2001). Studies in rat models of ischemic stroke induced by middle cerebral artery occlusion (MCAO) showed increased GSK-3β expression is following ischemia (Wang, et al., *Brain Res,* 859: 381, 2000; Sasaki, et al., *Neurol Res,* 23: 588, 2001). Fibroblast growth factor (FGF) reduced ischemic brain injury after permanent middle cerebral artery occlusion (MCO) in rats (Fisher, et al. 1995; Song, et al. 2002). Indeed, the neuroprotective effects of FGF demonstrated in ischemia models in rats may be mediated by a PI-3 kinase/AKT-dependent inactivation of GSK-3β (Hashimoto, et al., 2002). Thus, inhibition of GSK-3β after a cerebral ischemic event may ameliorate ischemic brain damage.

GSK-3 is also implicated in mycardial infarction. See Jonassen et al., *Circ Res,* 89:1191, 2001 (The reduction in myocardial infarction by insulin administration at reperfusion is mediated via Akt dependent signaling pathway); Matsui, et al., *Circulation,* 104:330, 2001 (Akt activation preserves cardiac function and prevents cardiomyocyte injury after transient cardiac ischemia in vivo); Miao, et al., *J Mol Cell Cardiol,* 32:2397, 2000 (Intracoronary, adenovirus-mediated Akt gene delivery in heart reduced gross infarct size following ischemia-reperfusion injury in vivo); and Fujio, et al., *Circulation,* 101:660, 2000 (Akt signaling inhibits cardiac myocyte apoptosis in vitro and protects against ischemia-reperfusion injury in mouse heart).

GSK-3 activity plays a role in head trauma. See Noshita, et al., *Neurobiol Dis,* 9:294, 2002 (Upregulation of Akt/PI3-kinase pathway may be crucial for cell survival after traumatic brain injury) and Dietrich, et al., *J Neurotrauma,* 13:309, 1996 (Posttraumatic administration of bFGF significantly reduced damaged cortical neurons & total contusion volume in a rat model of traumatic brain injury).

GSK-3 is also known to play a role in psychiatric disorders. See Eldar-Finkelman, *Trends Mol Med,* 8:126, 2002; Li, et al., *Bipolar Disord,* 4:137, 2002 (LiCl and Valproic acid, antipsychotic, mood stabilizing drugs, decrease GSK3 activities and increase beta-catenin) and Lijam, et al., *Cell,* 90:895, 1997 (Dishevelled KO mice showed abnormal social behavior and defective sensorimotor gating. Dishevelled, a cytoplamic protein involved in WNT pathway, inhibits GSK3beta activities).

It has been shown that GSK3 inhibition by lithium and valproic acid induces axonal remodeling and change synaptic connectivity. See Kaytor & Orr, *Curr Opin Neurobiol*, 12:275, 2002 (Downregulation of GSK3 causes changes in mirotubule-associated proteins: tau, MAP1 & 2) and Hall, et al., *Mol Cell Neurosci*, 20:257, 2002 (Lithium and valproic acid induces the formation of growth cone-like structures along the axons).

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells (Lovestone, et al., *Curr. Biol.*, 4:1077, 1994; and Brownlees et al., *Neuroreport* 8:3251, 1997; Kaytor and Orr, *Curr. Opin. Neurobiol.*, 12:275, 2000). In transgenic mice overexpressing GSK3, significant increased Tau hyperphosphorylation and abnormal morphology of neurons were observed (Lucas, et al., *EMBO J*, 20:27, 2001). Active GSK3 accumulates in cytoplasm of pretangled neurons, which can lead to neurofibrillary tangles in brains of patients with AD (Pei, et al., *J Neuropathol Exp Neurol*, 58:1010, 1999). Therefore, inhibition of GSK-3 slows or halts the generation of neurofibrillary tangles and thus treats or reduces the severity of Alzheimer's disease.

Evidence for the role GSK-3 plays in Alzheimer's disease has been shown in vitro. See Aplin, et al, *J Neurochem* 67:699, 1996; Sun, et al, *Neurosci Lett* 321:61, 2002 (GSK3b phosphorylates cytoplasmic domain of Amyloid Precursor Protein (APP) and GSK3b inhibition reduces Ab40 & Ab42 secretion in APP-transfected cells); Takashima, et al, *PNAS* 95:9637, 1998; Kirschenbaum, et al 2001, *J Biol Chem* 276: 7366, 2001 (GSK3b complexes with and phosphorylates presenilin-1, which is associated with gamma-secretase activity in the synthesis of Ab from APP); Takashima, et al, *Neurosci Res* 31:317, 1998 (Activation of GSK3b by Ab(25-35) enhances phosphorylation of tau in hippocampal neurons. This observation provides a link between Ab and neurofibrillary tangles composed of hyperphosphorylated tau, another pathological hallmark of AD); Takashima, et al, *PNAS* 90:7789, 1993 (Blockade of GSK3b expression or activity prevents Ab-induced neuro-degeneration of cortical and hippocampal primary cultures); Suhara, et al, *Neurobiol Aging*. 24:437, 2003 (Intracellular Ab42 is toxic to endothelial cells by interfering with activation of Akt/GSK-3b signaling-dependent mechanism); De Ferrari, et al *Mol Psychiatry* 8:195, 2003 (Lithium protects N2A cells & primary hippocampal neurons from Ab fibrils-induced cytotoxicity, & reduced nuclear translocation/destabilization of b-catenin); and Pigino, et al., *J Neurosci*, 23:4499, 2003 (The mutations in Alzheimer's presenilin 1 may deregulate and increase GSK-3 activity, which in turn, impairs axonal transport in neurons. The consequent reductions in axonal transport in affected neurons can ultimately lead to neurodegeneration).

Evidence for the role GSK-3 plays in Alzheimer's disease has been shown in vivo. See Yamaguchi, et al, *Acta Neuropathol* 92:232, 1996; Pei, et al, *J Neuropath Exp Neurol* 58:1010, 1999 (GSK3b immunoreactivity is elevated in susceptible regions of AD brains); Hernandez, et al, *J Neurochem* 83:1529, 2002 (Transgenic mice with conditional GSK3b overexpression exhibit cognitive deficits similar to those in transgenic APP mouse models of AD); De Ferrari, et al *Mol Psychiatry* 8:195, 2003 (Chronic lithium treatment rescued neurodegeneration and behavioral impairments (Morris water maze) caused by intrahippocampal injection of Ab fibrils.); McLaurin, et al., *Nature Med*, 8:1263, 2002 (Immunization with Ab in a transgenic model of AD reduces both AD-like neuropathology and the spatial memory impairments); and Phiel, et al *Nature* 423:435, 2003 (GSK3 regulates amyloid-beta peptide production via direct inhibition of gamma secretase in AD tg mice).

Presenilin-1 and kinesin-1 are also substrates for GSK-3 and relate to another mechanism for the role GSK-3 plays in Alzheimer's disease, as was recently described by Pigino, G., et al., *Journal of Neuroscience* (23:4499, 2003). It was found that GSK3beta phosphorylates kinsesin-I light chain, which results in a release of kinesin-1 from membrane-bound organelles, leading to a reduction in fast anterograde axonal transport (Morfini et al., 2002). The authors suggest that the mutations in PS1 may deregulate and increase GSK-3 activity, which in turn, impairs axonal transport in neurons. The consequent reductions in axonal transport in affected neurons ultimately lead to neurodegeneration.

GSK-3 is also associated with amyotrophic lateral sclerosis (ALS). See Williamson and Cleveland, 1999 (Axonal transport is retarded in a very early phase of ALS in mSOD1 mice); Morfini et al., 2002 (GSK3 phosphorylates kinesin light chains and inhibit anterograde axonal transport); Warita et al., *Apoptosis*, 6:345, 2001 (The majority of spinal motor neurons lost the immunoreactivities for both PI3-K and Akt in the early and presymptomatic stage that preceded significant loss of the neurons in this SOD1 tg animal model of ALS); and Sanchez, et al., 2001 (The inhibition of PI-3K induces neurite retraction mediated by GSK3 activation).

GSK-3 activity is also linked to spinal cord and peripheral nerve injuries. It has been shown that GSK3 inhibition by lithium and valproic acid can induce axonal remodeling and change synaptic connectivity. See Kaytor & Orr, *Curr Opin Neurobiol*, 12:275, 2002 (Downregulation of GSK3 causes changes in mirotubule-associated proteins: tau, MAP1 & 2) and Hall et al., *Mol Cell Neurosci*, 20:257, 2002 (Lithium and valproic acid induces the formation of growth cone-like structures along the axons). See also Grothe et al., *Brain Res*, 885:172, 2000 (FGF2 stimulate Schwann cell proliferation and inhibit myelination during axonal growth); Grothe and Nikkhah, 2001 (FGF-2 is up regulated in the proximal and distal nerve stumps within 5 hours after nerve crush); and Sanchez et al., 2001 (The inhibition of PI-3K induces neurite retraction mediated by GSK3 activation).

Another substrate of GSK-3 is β-catenin, which is degraded after phosphorylation by GSK-3. Reduced levels of β-catenin have been reported in schizophrenic patients and have also been associated with other diseases related to increase in neuronal cell death (Zhong et al., *Nature*, 395:698, 1998; Takashima et al., *PNAS*, 90:7789, 1993; Pei et al., *J. Neuropathol. Exp*, 56:70, 1997; and Smith et al., *Bioorg. Med. Chem.* 11:635, 2001). Furthermore, β-catenin and Tcf-4 play a dual role in vascular remodeling by inhibiting vascular smooth muscle cell apoptosis and promoting proliferation (Wang, et al., *Circ Res*, 90:340, 2002). Accordingly, GSK-3 is associated with angiogenic disorders. See also Liu, et al., *FASEB J*, 16:950, 2002 (Activation of GSK3 reduces hepatocyte growth factor, leading to altered endothelial cell barrier function and diminished vascular integrity) and Kim, et al., *J Biol Chem*, 277:41888, 2002 (GSK3beta activation inhibits angiogenesis in vivo using Matrigel plug assay: the inhibition of GSK3beta signaling enhances capillary formation).

Association between GSK-3 and Huntington's disease has been shown. See Carmichael et al., *J Biol Chem.*, 277:33791, 2002 (GSK3beta inhibition protect cells from polyglutamine-induced neuronal and non-neuronal cell death via increases in b-catenin and its associated transcriptional pathway). Overexpression of GSK3 reduced the activation of heat shock transcription factor-1 and heat shock protein HSP70 (Bijur et al., *J Biol Chem*, 275:7583, 2000) that are shown to decrease both poly-(Q) aggregates and cell death in in vitro HD model (Wyttenbach et al., *Hum Mol Genet*, 11:1137, 2002).

GSK-3 effects the levels of FGF-2 and their receptors are increased during remyelination of brain aggregate cultures remyelinating rat brains. See Copelman et al., 2000, Messersmith, et al., 2000; and Hinks and Franklin, 2000. It was also found that FGF-2 induces process outgrowth by oligodendrocytes implicating involvement of FGF in remyelination (Oh and Yong, 1996; Gogate et al., 1994) and that FGF-2 gene therapy has shown to improve the recovery of experimental allergic encephalomyelitis (EAE) mice (Ruffini, et al., 2001).

GSK-3 has also been associated with hair growth because Wnt/beta-catenin signaling is shown to play a major role in hair follicle morphogenesis and differentiation (Kishimotot et al. *Genes Dev*, 14:1181, 2000; Millar, *J Invest Dermatol*, 118:216, 2002). It was found that mice with constitutive overexpression of the inhibitors of Wnt signaling in skin failed to develop hair follicles. Wnt signals are required for the initial development of hair follicles and GSK3 constitutively regulates Wnt pathways by inhibiting beta-catenin. (Andl et al., *Dev Cell* 2:643, 2002). A transient Wnt signal provides the crucial initial stimulus for the start of a new hair growth cycle, by activating beta-catenin and TCF-regulated gene transcription in epithelial hair follicle precursors (Van Mater et al., *Genes Dev,* 17:1219, 2003)

Because GSK-3 activity is associated with sperm motility, GSK-3 inhibition is useful as a male contraceptive. It was shown that a decline in sperm GSK3 activity is associated with sperm motility development in bovine and monkey epididymis (Vijayaraghavan et al., *Biol Reprod*, 54: 709, 1996; Smith et al., *J Androl*, 20:47, 1999). Furthermore, tyrosine & serine/threonine phosphorylation of GSK3 is high in motile compared to immotile sperm in bulls (Vijayaraghavan et al., *Biol Reprod*, 62:1647, 2000). This effect was also demonstrated with human sperm (Luconi et al., *Human Reprod*, 16:1931, 2001).

Src Family Kinases

Another kinase family of particular interest is the Src family of kinases. These kinases are implicated in cancer, immune system dysfunction and bone remodeling diseases. For general reviews, see Thomas and Brugge, *Annu. Rev. Cell Dev. Biol.* 1997, 13, 513; Lawrence and Niu, *Pharmacol. Ther.* 1998, 77, 81; Tatosyan and Mizenina, *Biochemistry* (Moscow) 2000, 65, 49-58; Boschelli et al., *Drugs of the Future* 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 2000, 65, 49-58.

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell* 1992, 69, 551 and Soriano et al., *Cell* 1991, 64, 693.

Suppression of arthritic bone destruction has been achieved by the overexpression of CSK in rheumatoid synoviocytes and osteoclasts. Takayanagi et al., *J. Clin. Invest.* 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717.

Src also plays a role in the replication of hepatitis B virus. The virally encoded transcription factor HBx activates Src in a step required for propagation of the virus. Klein et al., *EMBO J.* 1999, 18, 5019, and Klein et al., *Mol. Cell. Biol.* 1997, 17, 6427.

A number of studies have linked Src expression to cancers such as colon, breast, hepatic and pancreatic cancer, certain B-cell leukemias and lymphomas. Talamonti et al., *J. Clin. Invest.* 1993, 91, 53; Lutz et al., *Biochem. Biophys. Res.* 1998 243, 503; Rosen et al., *J. Biol. Chem.* 1986, 261, 13754; Bolen et al., *Proc. Natl. Acad. Sci. USA* 1987, 84, 2251; Masaki et al., *Hepatology* 1998, 27, 1257; Biscardi et al., *Adv. Cancer Res.* 1999, 76, 61; Lynch et al., *Leukemia* 1993, 7, 1416. Furthermore, antisense Src expressed in ovarian and colon tumor cells has been shown to inhibit tumor growth. Wiener et al., *Clin. Cancer Res.*, 1999, 5, 2164; Staley et al., *Cell Growth Diff.* 1997, 8, 269.

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature*, 1992, 357, 161. Hck, Fgr and Lyn have been identified as important mediators of integrin signaling in myeloid leukocytes. Lowell et al., *J. Leukoc. Biol.*, 1999, 65, 313. Inhibition of these kinase mediators may therefore be useful for treating inflammation. Boschelli et al., *Drugs of the Future* 2000, 25(7), 717.

JNK Kinase

JNK is a member of the mitogen-activated protein (MAP) kinase family. MAP kinases (MAPKs) are activated by a variety of signals, including growth factors, cytokines, UV radiation, and stress-inducing agents. MAPKs are serine/threonine kinases and their activation occurs by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

Three distinct genes, JNK1, JNK2, JNK3 have been identified for this kinase family and at least ten different splicing isoforms of JNKs exist in mammalian cells (Gupta et al., *EMBO J.* 15:2760, 1996). Members of the JNK family are activated by proinflammatory cytokines, such as tumor necrosis factor-α (TNFα) and interleukin-1 β (IL-1β), as well as by environmental stress, including anisomycin, UV irradiation, hypoxia, and osmotic shock (Minden et al., *Biochemica et Biophysica Acta* 1333:F85, 1998).

The down-stream substrates of JNKs include transcription factors c-Jun, ATF-2, Elk1, p53, and a cell death domain protein (DENN) (Zhang et al. *Proc. Natl. Acad. Sci. USA* 1998, 95, 2586-91). Each JNK isoform binds to these substrates with different affinities, suggesting a regulation of signaling pathways by substrate specificity of different JNKs in vivo (Gupta et al., supra).

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer, and neurodegenerative diseases.

Several reports have detailed the importance of JNK activation associated with liver disease or episodes of hepatic ischemia (Behren, A. et al., *Nat. Genet.* 1999, 21, 326-9; Onishi, I. et al., *FEBS Lett.* 1997, 420, 201-4; Parola, M. et al., *J. Clin. Invest.* 1998, 102, 1942-50; Zwacka, R. M. et al., *Hepatology* 1998, 28, 1022-30). Therefore, inhibitors of JNK may be useful to treat various hepatic disorders.

A role for JNK in cardiovascular disease such as myocardial infarction or congestive heart failure has also been reported as it has been shown JNK mediates hypertrophic responses to various forms of cardiac stress (Adam, J. W. et al., *Circ. Res.* 1998, 83, 167-78; Kim, S. et al., *Circulation* 1998, 97, 1731-7; Liang, F. et al., *J. Biol. Chem.* 1997, 272, 28050-6; Bogoyevitch, M. A. et al., *Circ. Res.* 1996, 79, 162-73; Force, T. et al., *Circ. Res.* 1996, 78, 947-53; Xu, Q. et al., *J. Clin. Invest.* 1996, 97, 508-14).

It has been demonstrated that the JNK cascade also plays a role in T-cell activation, including activation of the IL-2 promoter. Thus, inhibitors of JNK may have therapeutic value in altering pathologic immune responses (Kempiak, S. et al., *J. Immunol.* 1999, 162, 3176-87; vanSeventer, G. A. et al., *Eur. J. Immunol.* 1998, 28, 3867-77; Dubois, B. et al., *J. Exp. Med.* 1997, 186, 941-53; Wilson, D. J. et al., *Eur. J. Immunol.* 1996, 26, 989-94).

A role for JNK activation in various cancers has also been established, suggesting the potential use of JNK inhibitors in cancer. For example, constitutively activated JNK is associated with HTLV-1 mediated tumorigenesis (Xu, X. et al., *Oncogene* 1996, 13, 135-42). JNK may play a role in Kaposi's sarcoma (KS) because it is thought that the proliferative effects of bFGF and OSM on KS cells are mediated by their activation of the JNK signaling pathway (Groopman, J. E. et al., *J. Clin. Invest.* 1997, 99, 1798-804). Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) (Burgess, G. M. et al., *Blood* 1998, 92, 2450-60).

JNK1 and JNK2 are widely expressed in a variety of tissues. In contrast, JNK3, is selectively expressed in the brain and to a lesser extent in the heart and testis (Gupta et al., supra; Mohit et al., *Neuron* 1995, 14, 67-78; Martin et al., *Brain Res. Mol. Brain Res.* 1996, 35, 47-57). JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex (Mohit et al., supra). The CA1 neurons of patients with acute hypoxia showed strong nuclear JNK3-immunoreactivity compared to minimal, diffuse cytoplasmic staining of the hippocampal neurons from brain tissues of normal patients (Zhang et al., supra). Thus, JNK3 appears to be involved involved in hypoxic and ischemic damage of CA1 neurons in the hippocampus.

In addition, JNK3 co-localizes immunochemically with neurons vulnerable in Alzheimer's disease (Mohit et al., supra). Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., *Nature* 1997, 389, 865-870).

Based on these findings, JNK signalling, especially that of JNK3, has been implicated in the areas of apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke.

Accordingly, there is a great need to develop compounds useful as inhibitors of protein kinases. In particular, it would be desirable to develop compounds that are useful as inhibitors of ERK2, JNK3, Src, Aurora2, and GSK3 protein kinases particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of one or more of ERK2, JNK3, Src, Aurora2, and GSK3 protein kinases. These compounds have the general formula I:

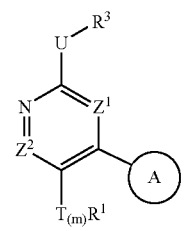

I or a pharmaceutically acceptable salt thereof, wherein Ring A, $Z^1$, $Z^2$, T, m, U, $R^1$, and $R^3$ are as defined below.

These compounds, and pharmaceutically acceptable compositions thereof, are useful for treating or preventing a variety of diseases, disorders or conditions, including, but not limited to, cancer, heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, neurodegenerative or neurological disorders, or viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

1. General Description of Compounds of the Invention

The present invention relates to a compound of formula I:

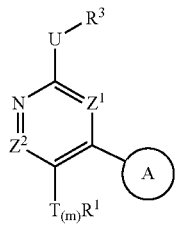

or a pharmaceutically acceptable salt thereof, wherein:

Ring A is a pyrrole ring optionally substituted at the 1-position with $R^z$ and substituted with:
  (i) two $R^y$ groups, and
  (ii) $QR^2$;

$R^z$ is R, C(O)R, C(O)OR, or $SO_2R$;

each $R^y$ is independently selected from an optionally substituted $C_{1-6}$ aliphatic group, Ar, CN, $NO_2$, halogen, $N(R)_2$, SR, or OR, provided that both $R^y$ groups are not simultaneously Ar;

$Z^1$ and $Z^2$ are each independently selected from N or $CR^x$;

each $R^x$ is independently selected from R, halogen, CN, $NO_2$, OR, SR, $N(R)_2$, C(O)R, or $CO_2R$;

U is selected from a valence bond, —O—, —S—, —N(R)—, or a $C_{1-6}$ alkylidene chain wherein up to two methylene units of U are optionally and independently replaced by —O—, —S—, —SO—, —$SO_2$—, —N(R)$SO_2$—, —$SO_2$N(R)—, —N(R)—, —CO—, —$CO_2$—, —N(R)CO—, —N(R)C(O)O—, —N(R)CON(R)—, —N(R)$SO_2$N(R)—, —N(R)N(R)—, —C(O)N(R)—, or —OC(O)N(R)—;

T is a valence bond or a $C_{1-6}$ alkylidene chain;

m is zero or one;

$R^1$ is selected from CN, halogen, $OR^6$, $SR^6$, $N(R)R^6$, or $R^4$;

Q is selected from a valence bond, —C(O)N(R)—, —$SO_2$N(R)—, —$SO_2$—, —N(R)C(O)N(R)—, —N(R)C(O)—, —N(R)$SO_2$—, —N(R)$SO_2$N(R)—, —N(R)C(O)O—, —C(O)—, or —C(O)O—;

$R^2$ is selected from halogen, CN, $(CH_2)_yR^5$, $(CH_2)_yCH(R^5)_2$, $(CH_2)_yCH(R^7)CH(R^5)_2$, $(CH_2)_yN(R^4)_2$, or $N(R^4)(CH_2)_yN(R^4)_2$;

y is 0-6;

each Ar is independently selected from an optionally substituted 3-7 membered saturated, partially unsaturated, or fully unsaturated monocyclic ring having 0-4 heteroatoms independently selected from nitrogen, oxygen, or sulfur, or an optionally substituted 8-10 membered saturated, partially unsaturated, or fully unsaturated bicyclic ring having 0-4 heteroatoms independently selected from nitrogen, oxygen, or sulfur;

$R^3$ is selected from R, Ar, $(CH_2)_yCH(R^7)R^5$, CN, $(CH_2)_yCH(R^7)CH(R^5)_2$, or $(CH_2)_yCH(R^7)N(R^4)_2$;

each R is independently selected from hydrogen or an optionally substituted $C_{1-6}$ aliphatic group, or:
  two R on the same nitrogen atom are taken together with the nitrogen atom attached thereto to form a 4-8 membered saturated, partially unsaturated, or fully unsaturated ring having 1-4 heteroatoms independently selected from nitrogen, oxygen, or sulfur;

each $R^4$ is independently selected from $R^6$, $C(O)R^6$, $CO_2R^6$, $CON(R^6)_2$, $SO_2R^6$;

each $R^5$ is independently selected from $R^6$, $OR^6$, $CO_2R^6$, $(CH_2)_yN(R^4)_2$, $N(R^4)_2$, $N(R)C(O)R^6$, $N(R)CON(R^6)_2$, $CON(R^6)_2$, $SO_2R^6$, $N(R)SO_2R^6$, $C(O)R^6$, CN, or $SO_2N(R^6)_2$;

each $R^6$ is independently selected from R or Ar;

$R^7$ is selected from $R^6$, $(CH_2)_wOR^6$, $(CH_2)_wN(R^4)_2$, or $(CH_2)_wSR^6$; and each w is independently selected from 0-4;

provided that:

when $R^1$ is hydrogen, U is —NH—, and $R^3$ is an optionally substituted phenyl ring, then Q is other than a valence bond.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; $R°$; $OR°$; $SR°$; 1,2-methylene-dioxy; 1,2-ethylenedioxy; phenyl (Ph) optionally substituted with $R°$; —O(Ph) optionally substituted with $R°$; $(CH_2)_{1-2}$(Ph), optionally substituted with $R°$; CH=CH(Ph), optionally substituted with $R°$; $NO_2$; CN; $N(R°)_2$; $NR°C(O)R°$; $NR°C(O)N(R°)_2$; $NR°CO_2R°$; —$NR°NR°C(O)R°$; $NR°NR°C(O)N(R°)_2$; $NR°NR°CO_2R°$; $C(O)C(O)R°$; $C(O)CH_2C(O)R°$; $CO_2R°$; $C(O)R°$; $C(O)N(R°)_2$; $OC(O)N(R°)_2$; $S(O)_2R°$; $SO_2N(R°)_2$; $S(O)R°$; $NR°SO_2N(R°)_2$; $NR°SO_2R°$; $C(=S)N(R°)_2$; $C(=NH)$—$N(R°)_2$; or $(CH_2)_{0-2}NHC(O)R°$ wherein each independent occurrence of $R°$ is selected from hydrogen, optionally substituted $C_{1-6}$ aliphatic, an unsubstituted 5-6 membered heteroaryl or heterocyclic ring, phenyl, O(Ph), or $CH_2$(Ph), or, notwithstanding the definition above, two independent occurrences of $R°$, on the same substituent or different substituents, taken together with the atom(s) to which each $R°$ group is bound, form a 3-8 membered cycloalkyl, heterocyclyl, aryl, or heteroaryl ring having 0-3 heteroatoms independently selected from nitrogen, oxygen, or sulfur. Optional substituents on the aliphatic group of $R°$ are selected from $NH_2$, $NH(C_{1-4}$aliphatic), $N(C_{1-4}$aliphatic)$_2$, halogen, $C_{1-4}$aliphatic, OH, $O(C_{1-4}$aliphatic), $NO_2$, CN, $CO_2H$, $CO_2(C_{1-4}$aliphatic), $O(haloC_{1-4}$ aliphatic), or halo$C_{1-4}$aliphatic, wherein each of the foregoing $C_{1-4}$aliphatic groups of $R°$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O) R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(halo C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from $R^+$, $N(R^+)_2$, $C(O)R^+$, $CO_2R^+$, $C(O)C(O)R^+$, $C(O)CH_2C(O)R^+$, $SO_2R^+$, $SO_2N(R^+)_2$, $C(=S)N(R^+)_2$, $C(=NH)$—$N(R^+)_2$, or $NR^+SO_2R^+$; wherein $R^+$ is hydrogen, an optionally substituted $C_{1-6}$ aliphatic, optionally substituted phenyl, optionally substituted O(Ph), optionally substituted $CH_2$(Ph), optionally substituted $(CH_2)_{1-2}$(Ph); optionally substituted CH=CH (Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(halo C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of $R^o$ (or $R^+$, or any other variable similarly defined herein), are taken together together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of $OR^o$

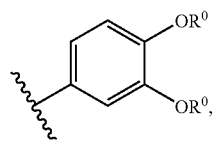

these two occurrences of $R^o$ are taken together with the oxygen atoms to which they are bound to form a fused 6-membered oxygen containing ring:

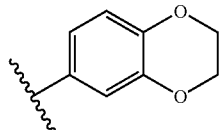

It will be appreciated that a variety of other rings can be formed when two independent occurrences of $R^o$ (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. Such compounds are useful, for example, as analytical tools or probes in biological assays.

3. Description of Exemplary Compounds:

According to one embodiment, the present invention relates to a compound of formula I wherein $Z^1$ is nitrogen and $Z^2$ is $CR^x$, thus forming a pyrimidine ring. Accordingly, the present invention relates to a compound of formula I-a:

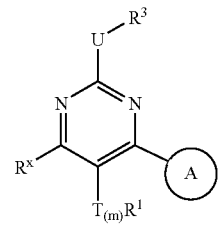

I-a or a pharmaceutically acceptable salt thereof, wherein Ring A, U, $R^x$, T, m, $R^1$, and $R^3$ are as defined above.

According to another embodiment, the present invention relates to a compound of formula I wherein $Z^1$ and $Z^2$ are each $CR^x$, thus forming a pyridine ring. Accordingly, the present invention relates to a compound of formula I-b:

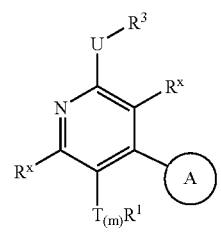

I-b or a pharmaceutically acceptable salt thereof, wherein Ring A, U, $R^x$, T, m, $R^1$, and $R^3$ are as defined above.

According to yet another embodiment, the present invention relates to a compound of formula I wherein $Z^1$ and $Z^2$ are each nitrogen, thus forming a 1,2,5-triazine ring. Accordingly, the present invention relates to a compound of formula I-c:

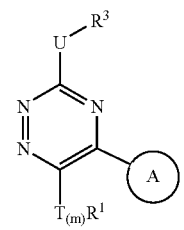

I-c or a pharmaceutically acceptable salt thereof, wherein Ring A, U, T, m, $R^1$, and $R^3$ are as defined above.

In certain embodiments, the $R^x$ groups of any of formulae I, I-a, I-b, or I-c are independently selected from hydrogen, OH, or halogen.

In certain other embodiments, the $R^x$ groups of any of formulae I, I-a, I-b, or I-c are each hydrogen.

According to one embodiment, the $T_{(m)}R^1$ group of any of formulae I, I-a, I-b, or I-c is selected from hydrogen, $N(R)R^6$, $OR^6$, 3-6 membered carbocyclyl, or an optionally substituted group selected from $C_{1-6}$ aliphatic or a 5-6 membered aryl ring having 0-4 heteroatoms independently selected from nitrogen, oxygen, or sulfur. When $R^1$ is an optionally substituted phenyl or $C_{1-6}$ aliphatic group, exemplary substituents on the phenyl or $C_{1-6}$ aliphatic group include $R^o$, halo, nitro, $OR^o$, and amino. Another embodiment of the present invention relates to a compound of any of formulae I, I-a, I-b, or I-c wherein $T_{(m)}R^1$ is hydrogen, methyl, ethyl, propyl, cyclopropyl, cyclohexyl, phenyl, pyridyl, $CH_2OCH_3$, $CH_2OH$, $NH_2$, $NHCH_3$, $NHAc$, $NHC(O)NHCH_3$, or $CH_2NHCH_3$.

In certain embodiments, the T moiety of any of formulae I, I-a, I-b, or I-c is a valence bond.

In other embodiments, the T moiety of any of formulae I, I-a, I-b, or I-c is —$CH_2$—.

Another embodiment of the present invention relates to a compound of any of formulae I, I-a, I-b, or I-c wherein $R^3$ is hydrogen, 3-7 membered carbocyclyl or an optionally substituted group selected from $C_{1-4}$ aliphatic, a 3-6 membered heterocyclic ring having 1-3 heteroatoms independently selected from nitrogen, oxygen, or sulfur, or a 5-6 membered aryl or heteroaryl ring having 1-3 heteroatoms independently selected from nitrogen, oxygen, or sulfur. Examples of such groups include methyl, ethyl, propyl, cyclopropyl, cyclohexyl, benzyl, isoxazolyl, tetrahydrofuranyl, and isopropyl. According to another embodiment, when $R^3$ is optionally substituted phenyl, substituents on the phenyl ring include halogen, $R^o$, $OR^o$, $N(R^o)_2$, $SO_2N(R^o)_2$. Examples of such substituents include haloalkyl, Obenzyl, Ophenyl, $OCF_3$, OH, $SO_2NH_2$, and methylene dioxy.

When the $R^3$ moiety of any of formulae I, I-a, I-b, or I-c is $CH(R^7)R^5$, examples of such groups include $CH(CH_2OH)$phenyl, $CH(CH_2OH)$ethyl, $CH(CH_2OH)_2$, $CH(CH_2OH)$isopropyl, and $CH(CH_2OH)CH_2$cyclopropyl.

When the $R^3$ moiety of any of formulae I, I-a, I-b, or I-c is a 3-6 membered heterocyclic ring having 1-3 heteroatoms independently selected from nitrogen, oxygen, or sulfur, examples of such groups include piperazin-1-yl, morpholin-4-yl, or piperidin-1-yl.

According to another embodiment, the U group of any of formulae I, I-a, I-b, or I-c is a valence bond, —$CH_2$—, —O—, —NR—, —NHCO—, or —$NHCO_2$—.

In certain embodiments of the present invention, the U group of any of formulae I, I-a, I-b, or I-c is a valence bond.

In other embodiments of the present invention, the U group of any of formulae I, I-a, I-b, or I-c is —NH—.

Yet another embodiment of the present invention relates to a compound of any of formulae I, I-a, I-b, or I-c wherein U is —O—.

Another embodiment relates to a compound of any of formulae I, I-a, I-b, or I-c wherein $R^2$ is selected from $(CH_2)_yR^5$, $(CH_2)_yCH(R^5)_2$, $(CH_2)_yCH(R^7)CH(R^5)_2$, or $(CH_2)_yN(R^4)_2$. According to another embodiment, the $R^2$ group of of any of formulae I, I-a, I-b, or I-c is $(CH_2)_yR^5$, $(CH_2)_yCH(R^5)_2$, or $(CH_2)_yCH(R^7)CH(R^5)_2$.

When $R^2$ is $R^5$, $R^5$ groups include an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such groups are pyrrolidin-1-yl, morpholin-4-yl, piperidin-1-yl, and piperazin-1-yl, 4-methyl[1,4]diazepan-1-yl, 4-phenyl-piperazine-1-yl, wherein each group is optionally substituted.

When $R^2$ is $(CH_2)_yR^5$, $(CH_2)_yCH(R^5)_2$, or —$N(R^4)_2$, $R^5$ groups are further selected from pyridin-3-yl, pyridin-4-yl, imidazolyl, furan-2-yl, 1,2,3,4-tetrahydroisoquinoline, tetrahydrofuran-2-yl, cyclohexyl, phenyl, benzyl, $CH_2OH$, $(CH_2)_2OH$, and isopropyl, wherein each group is optionally substituted. Examples of substituents on $R^5$ include OH, pyridyl, piperidinyl, and optionally substituted phenyl.

When $R^2$ is $(CH_2)_yCH(R^5)_2$, $R^5$ groups are selected from $R^6$, $OR^6$, $CO_2R^6$, $(CH_2)N(R^4)_2$, or CN. The $R^5$ group of the $R^2$ moiety of any of formulae I, I-a, I-b, or I-c are also independently selected from $R^6$, $OR^6$, $CO_2R^6$, $(CH_2)N(R^4)_2$, CN, an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^5$ groups include optionally substituted groups selected from phenyl, pyridyl, morpholin-4-yl, imidazolyl, OH, and $CH_2OH$.

When $R^2$ is $(CH_2)_yCH(R^7)CH(R^5)_2$, $R^7$ groups are selected from $R^6$, $(CH_2)_wOR^6$, or $(CH_2)_wN(R^4)_2$. According to another embodiment, the $R^7$ group of the $R^2$ moiety of any of formulae I, I-a, I-b, or I-c is selected from $R^6$ or $(CH_2)_wOR^6$. According to yet another embodiment, the $R^7$ group of the $R^2$ moiety of any of formulae I, I-a, I-b, or I-c is selected from OH, $CH_2OH$, $(CH_2)_2OH$. The $R^5$ groups of the $(CH_2)_yCH(R^7)CH(R^5)_2$ moiety are independently selected from $R^6$, $OR^6$, Ar, $CO_2R^6$, $(CH_2)_yN(R^4)_2$, or CN. According to another embodiment, said $R^5$ groups are independently selected from $R^6$, $OR^6$, $CO_2R^6$, $(CH_2)_yN(R^6)_2$, CN, an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^5$ groups include optionally substituted groups selected from phenyl, pyridyl, morpholin-4-yl, imidazolyl, OH, and $CH_2OH$.

According to another embodiment, the $R^y$ groups of any of formulae I, I-a, I-b, or I-c are independently selected from $C_{1-4}$ aliphatic or Ar, wherein Ar is an optionally substituted 3-6 membered saturated, partially unsaturated, or fully unsaturated monocyclic ring having 0-4 heteroatoms independently selected from nitrogen, oxygen, or sulfur, or an optionally substituted 9-10 membered saturated, partially unsaturated, or fully unsaturated bicyclic ring having 0-4 heteroatoms independently selected from nitrogen, oxygen, or sulfur. Another embodiment relates to compounds of any of formulae I, I-a, I-b, or I-c wherein the $R^y$ groups are selected from $C_{1-4}$ aliphatic or Ar, wherein Ar is an optionally substituted 5-6 membered saturated, partially unsaturated, or fully unsaturated monocyclic ring having 0-4 heteroatoms independently selected from nitrogen, oxygen, or sulfur. Examples of such groups include phenyl, pyridyl, methyl, cyclohexyl, cyclopentyl, or ethyl.

Another embodiment of the present invention relates to a compound of any of formulae I, I-a, I-b, or I-c wherein $R^z$ includes hydrogen, optionally substituted $C_{1-4}$ aliphatic, C(O)R, and C(O)OR. According to another embodiment, $R^z$ is hydrogen, methyl, ethyl, C(O)Me, C(O)OCH$_2$phenyl, and CH$_2$phenyl. According to yet another embodiment, the $R^z$ group of any of formulae I, I-a, I-b, or I-c is hydrogen.

According to one embodiment, the Q group of of any of I, I-a, I-b, or I-c is selected from —C(O)N(R)— and —C(O)O—. According to another embodiment, Q group of any of formulae I, I-a, I-b, or I-c is selected from —C(O)N(H)— and —C(O)O—.

According to one embodiment, the present invention relates to a compound of of any of formulae I, I-a, I-b, or I-c wherein Q is —C(O)N(H)—.

According to another embodiment, the present invention relates to a compound of any of formulae I, I-a, I-b, or I-c wherein Q is —C(O)O—.

According to yet another embodiment, the present invention relates to a compound of any of formulae I, I-a, I-b, or I-c wherein $T_{(m)}R^1$ is other than hydrogen.

According to another embodiment, the present invention relates to a compound of formula II:

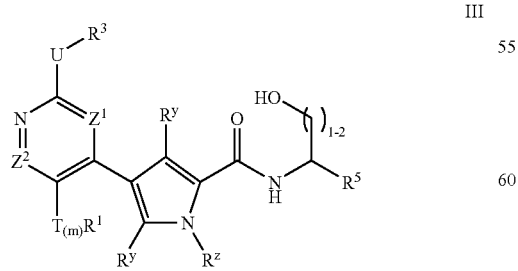

II or a pharmaceutically acceptable salt thereof, wherein $Z^1$, $Z^2$, $Z^3$, Q, U, $R^y$, $R^z$, $R^2$, and $R^3$ are as defined above.

Embodiments, and sub-embodiments thereof, relating to the $Z^1$, $Z^2$, $Z^3$, Q, U, $R^y$, $R^z$, $R^2$, and $R^3$ groups of formula II are those set forth above for compounds of formula I.

According to another embodiment, the present invention relates to a compound of formula III:

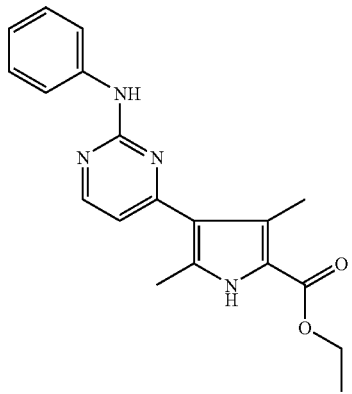

III or a pharmaceutically acceptable salt thereof, wherein $Z^1$, $Z^2$, $Z^3$, U, $R^y$, $R^z$, $R^3$, and $R^5$ are as defined above.

Embodiments, and sub-embodiments thereof, relating to the $Z^1$, $Z^2$, $Z^3$, U, $R^y$, $R^z$, $R^3$, and $R^5$ groups of formula III are those described above for compounds of formula I.

According to another embodiment, the present invention relates to a compound of formula IV:

IV or a pharmaceutically acceptable salt thereof, wherein $Z^1$, $Z^2$, $Z^3$, U, $R^y$, $R^z$, $R^3$, $R^5$, and $R^7$ are as defined above.

Embodiments, and sub-embodiments thereof, relating to the $Z^1$, $Z^2$, $Z^3$, U, $R^y$, $R^z$, $R^3$, $R^5$, and $R^7$ groups of formula IV are those described above for compounds of formula I.

Representative compounds of formula I are set forth in Table 1 below.

TABLE 1

Examples of Compounds of Formula I:

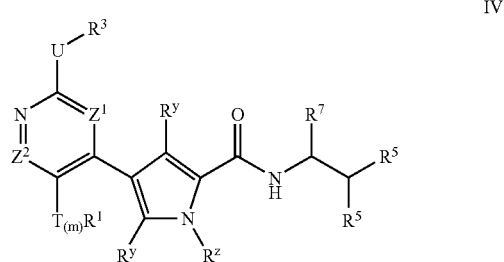

I-1

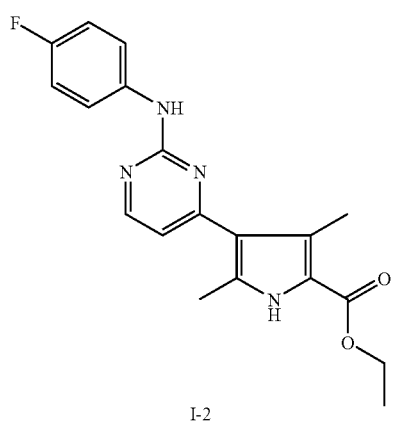

I-2

TABLE 1-continued
Examples of Compounds of Formula I:
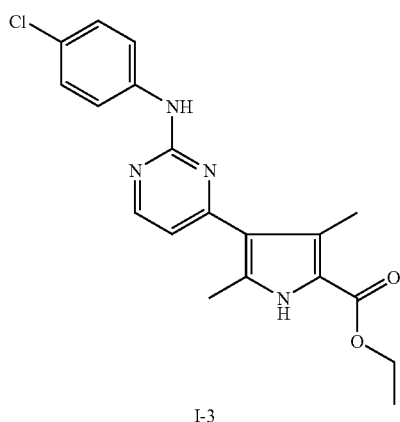
I-3
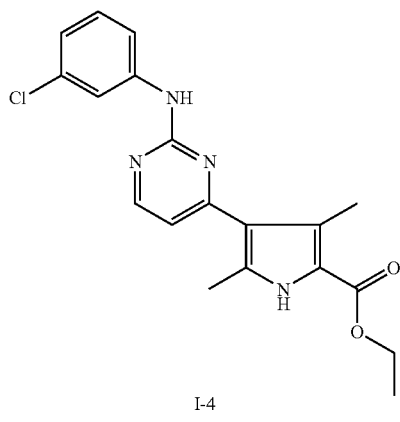
I-4
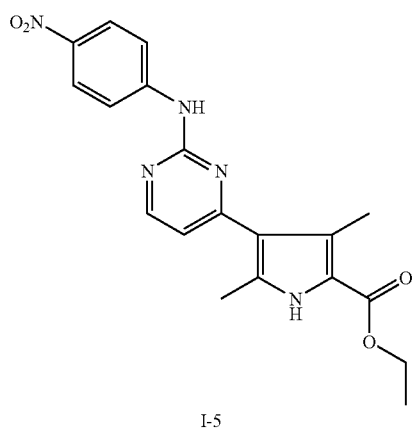
I-5
TABLE 1-continued
Examples of Compounds of Formula I:
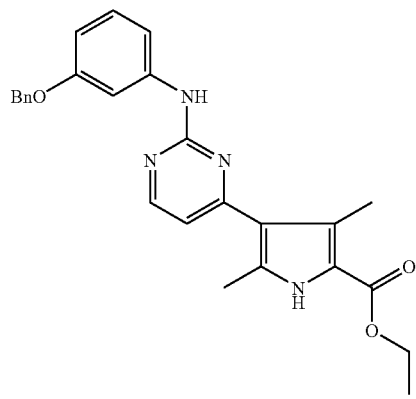
I-6
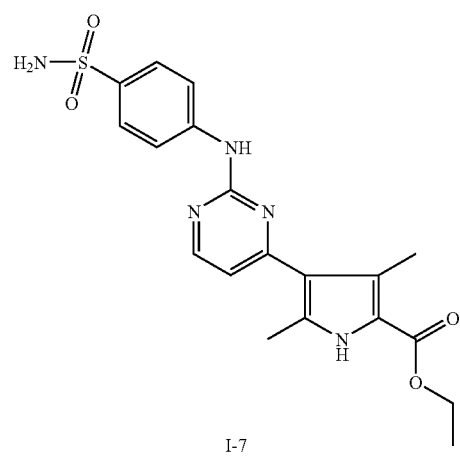
I-7
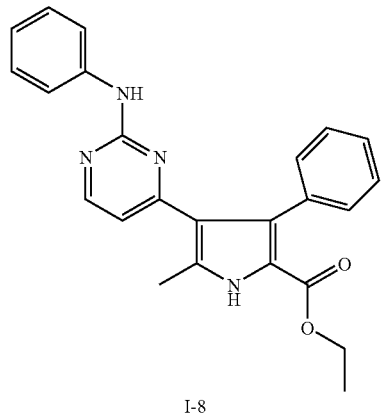
I-8

TABLE 1-continued
Examples of Compounds of Formula I:
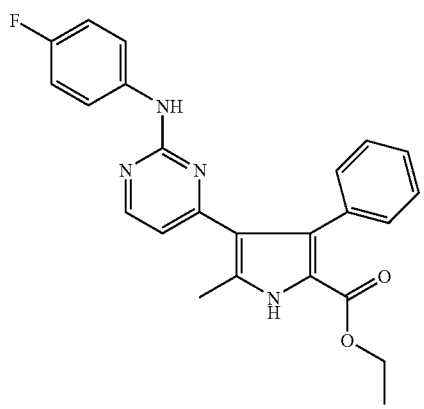
I-9
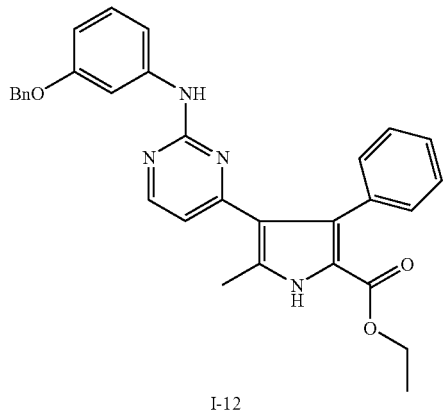
I-12
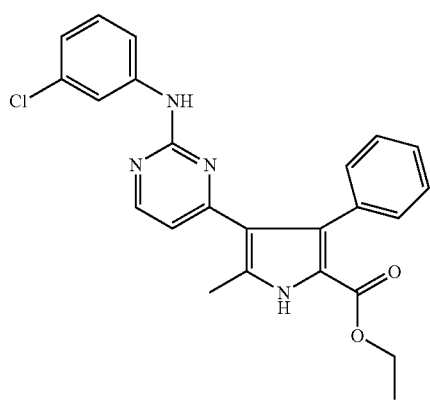
I-10
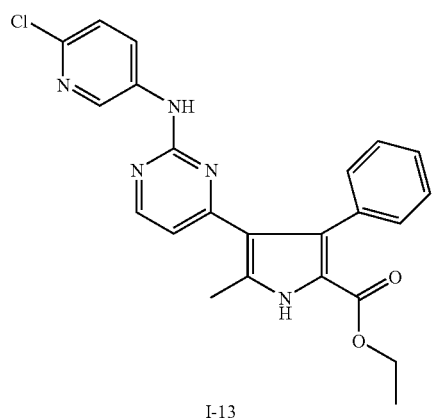
I-13
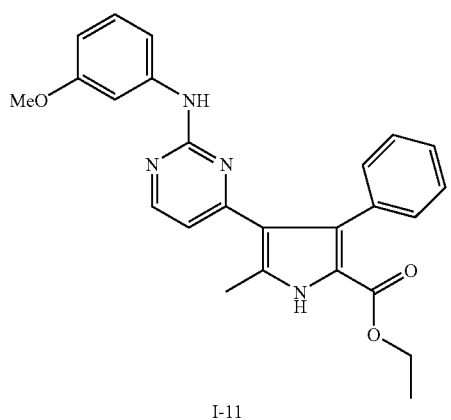
I-11
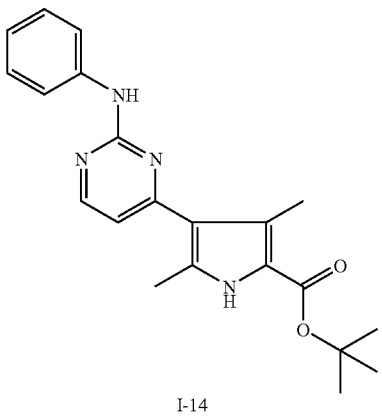
I-14

TABLE 1-continued
Examples of Compounds of Formula I:
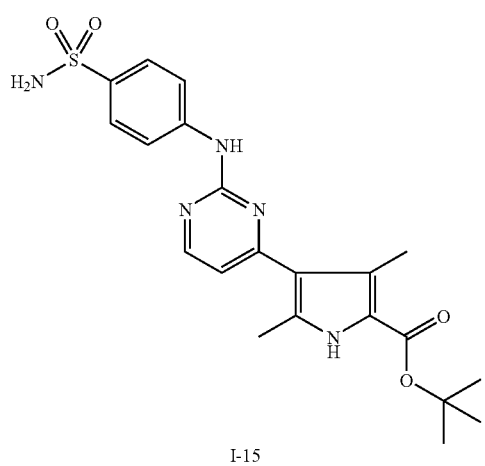
I-15
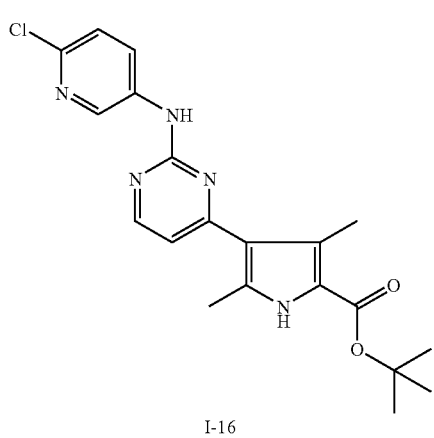
I-16
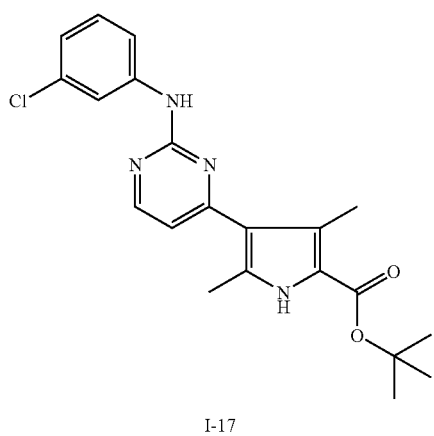
I-17
TABLE 1-continued
Examples of Compounds of Formula I:
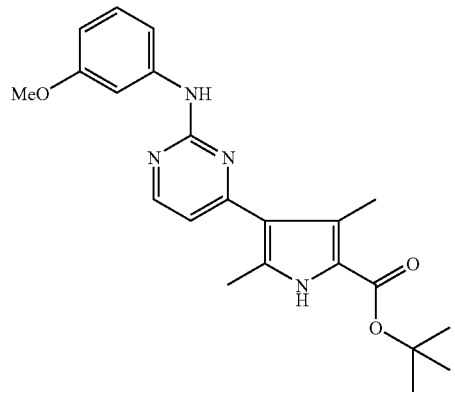
I-18
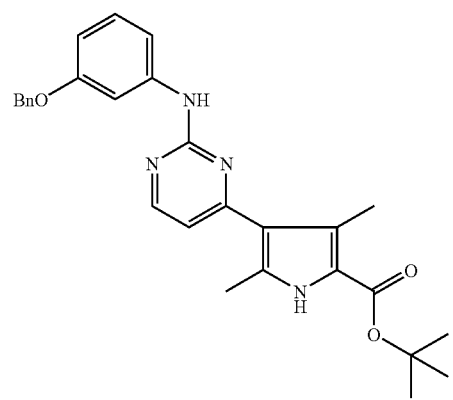
I-19
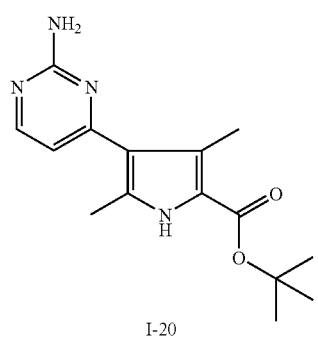
I-20

TABLE 1-continued

Examples of Compounds of Formula I:

I-21

I-22

I-23

I-24

I-25

I-26

I-27

TABLE 1-continued
Examples of Compounds of Formula I:
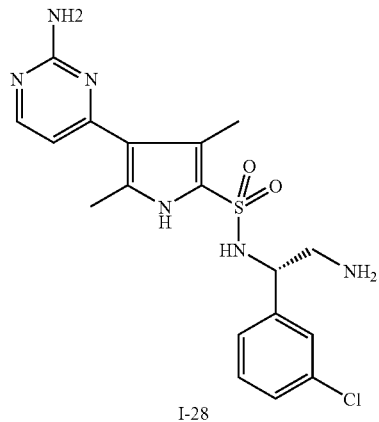
I-28
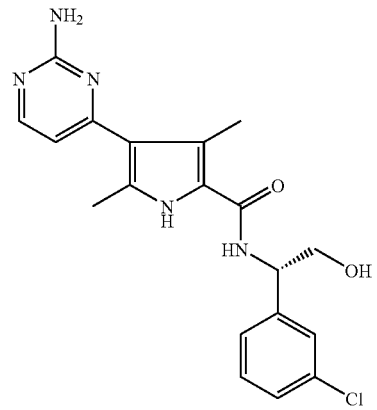
I-31
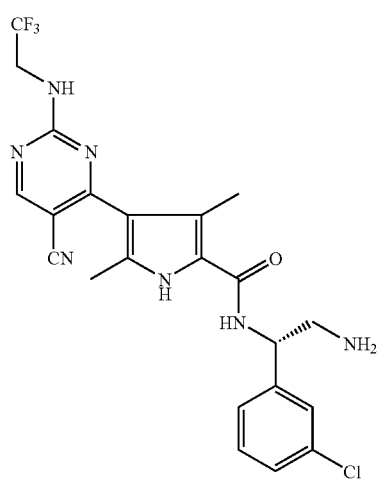
I-29
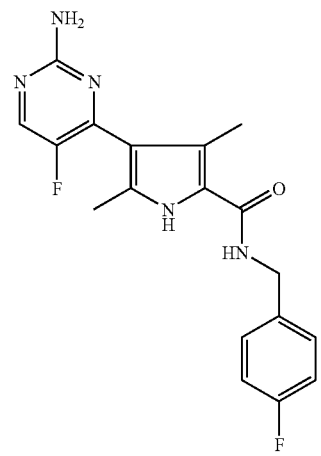
I-32
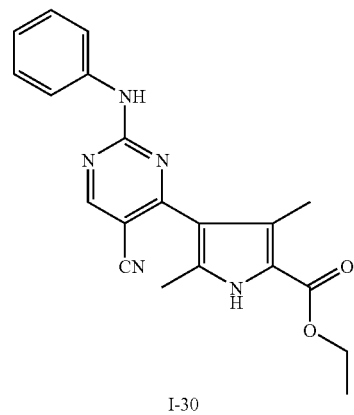
I-30
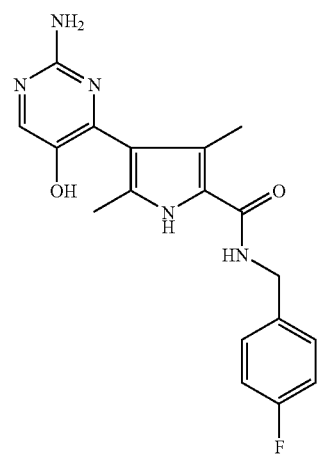
I-33

TABLE 1-continued
Examples of Compounds of Formula I:
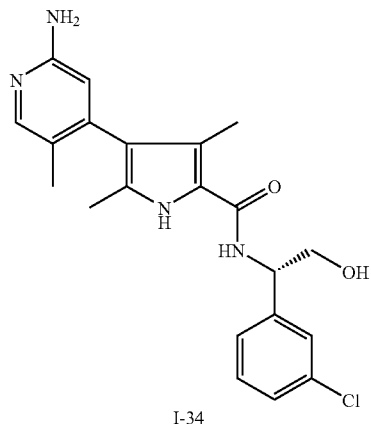
I-34
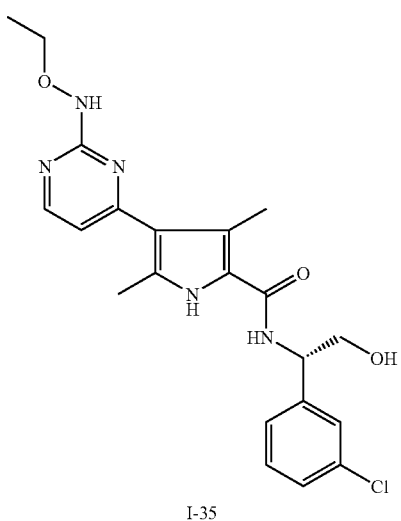
I-35
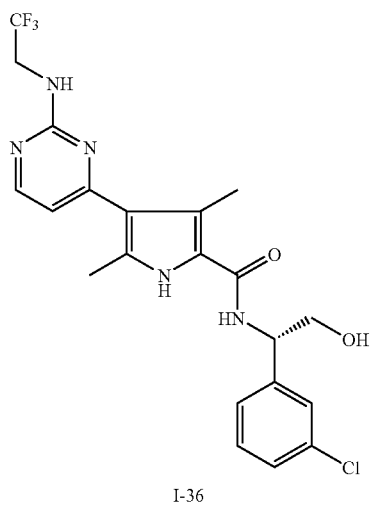
I-36
TABLE 1-continued
Examples of Compounds of Formula I:
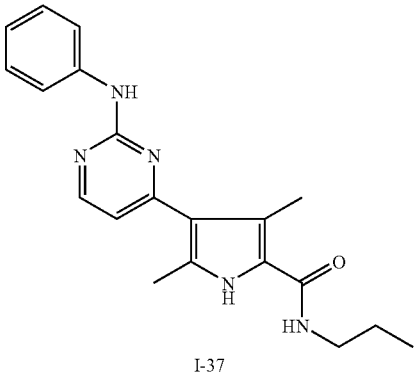
I-37
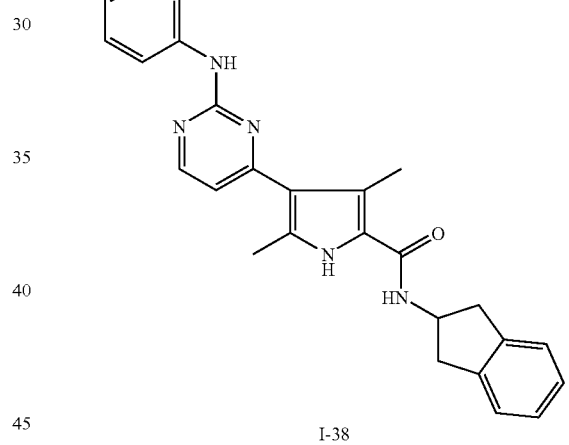
I-38
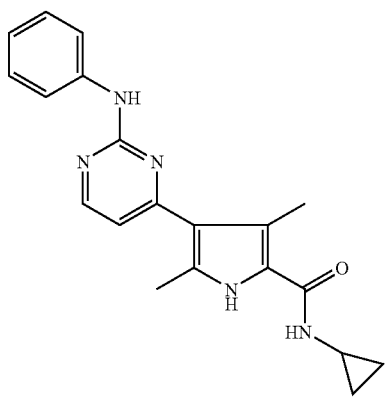
I-39

TABLE 1-continued
Examples of Compounds of Formula I:
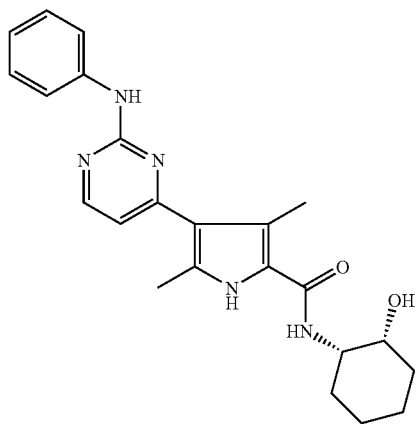
I-40
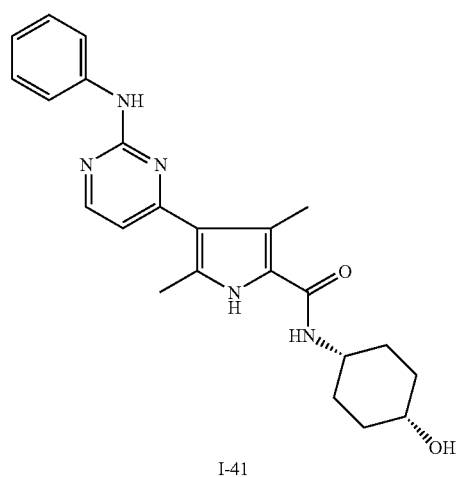
I-41
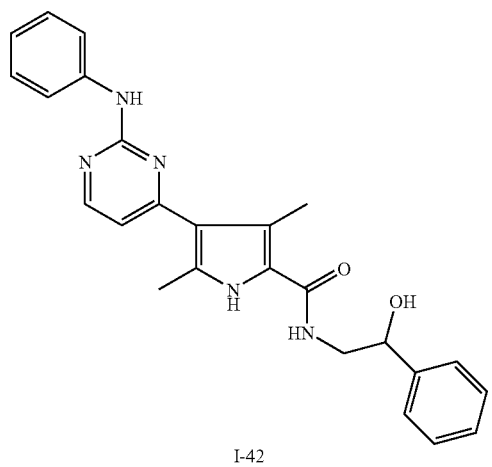
I-42
TABLE 1-continued
Examples of Compounds of Formula I:
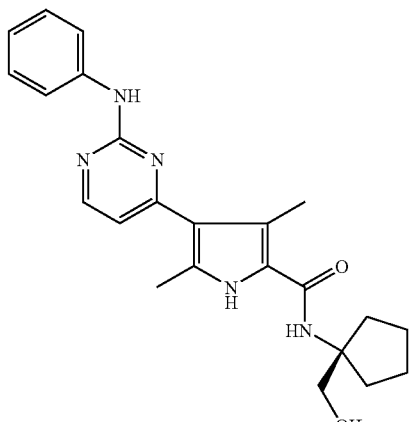
I-43
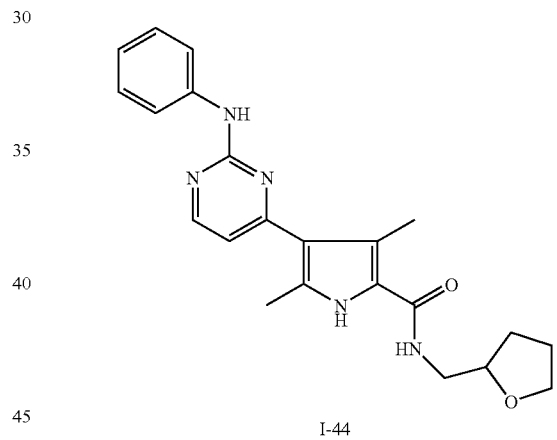
I-44
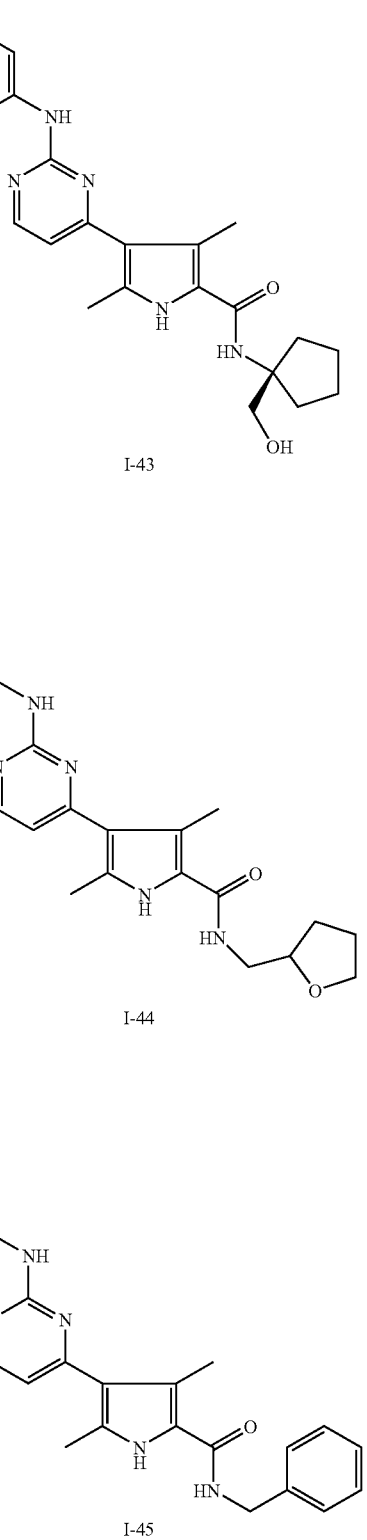
I-45

TABLE 1-continued
Examples of Compounds of Formula I:
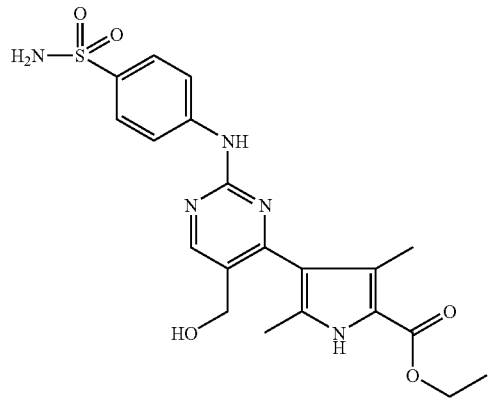
I-46
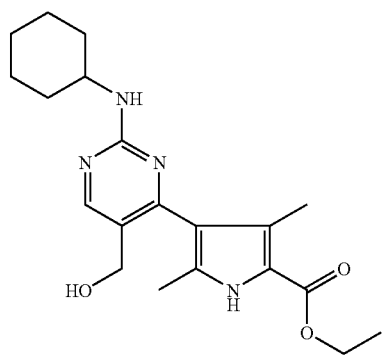
I-47
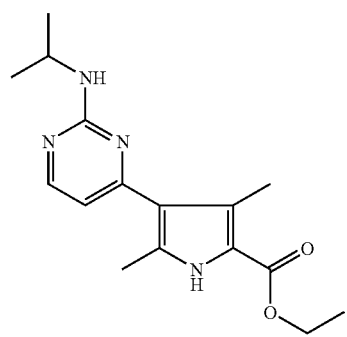
I-48
TABLE 1-continued
Examples of Compounds of Formula I:
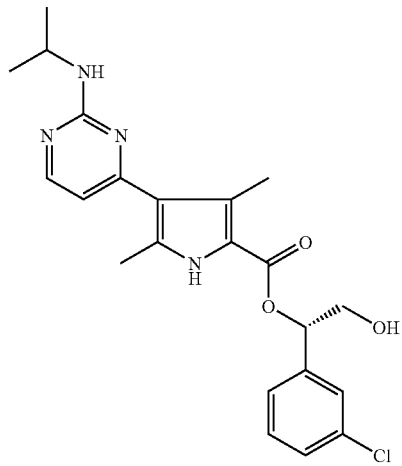
I-49
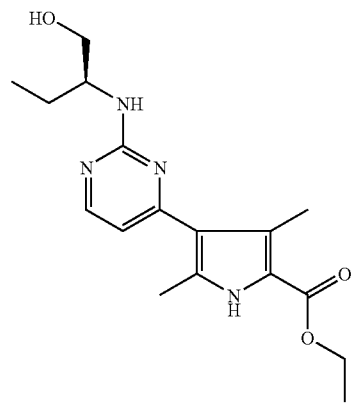
I-50
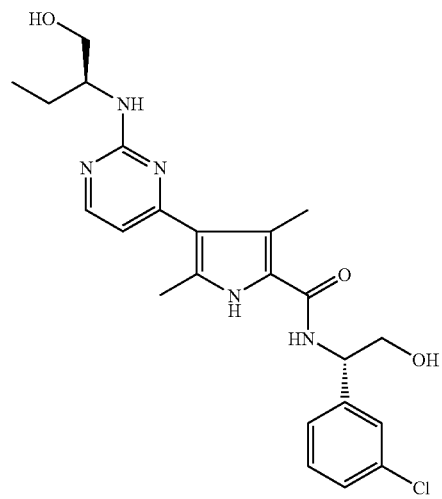
I-51

TABLE 1-continued
Examples of Compounds of Formula I:
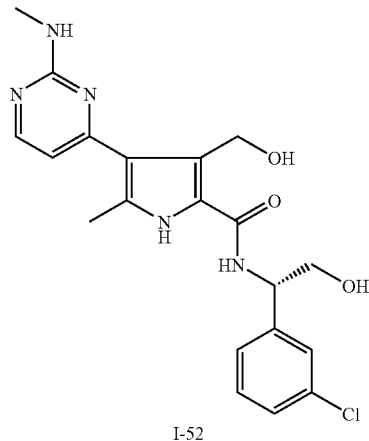
I-52
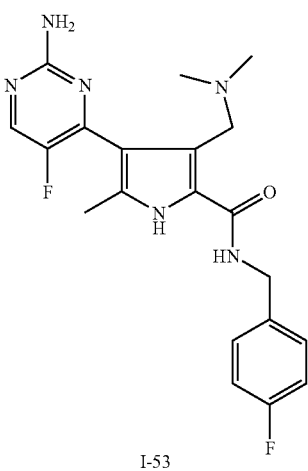
I-53
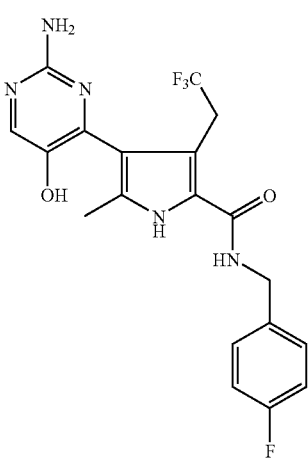
I-54
TABLE 1-continued
Examples of Compounds of Formula I:
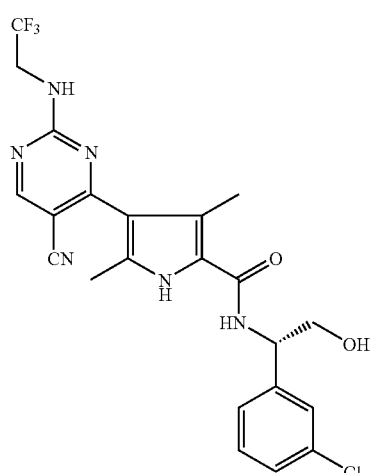
I-55
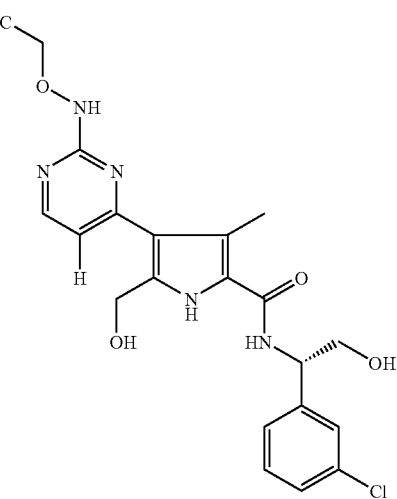
I-56
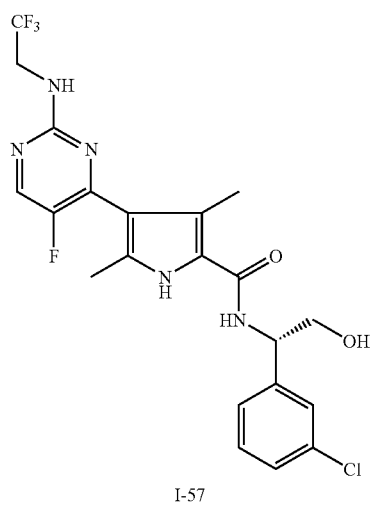
I-57

TABLE 1-continued
Examples of Compounds of Formula I:
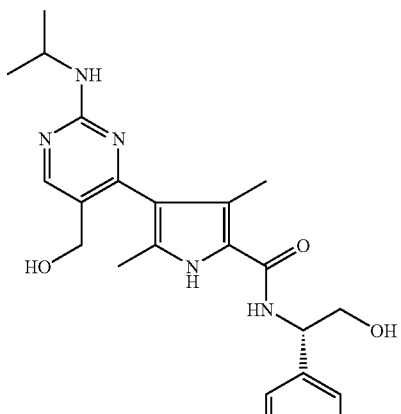
I-58
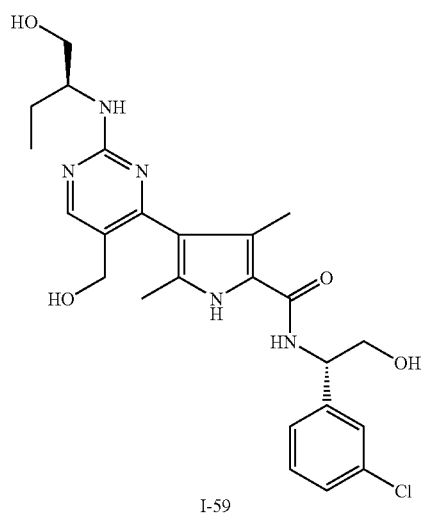
I-59
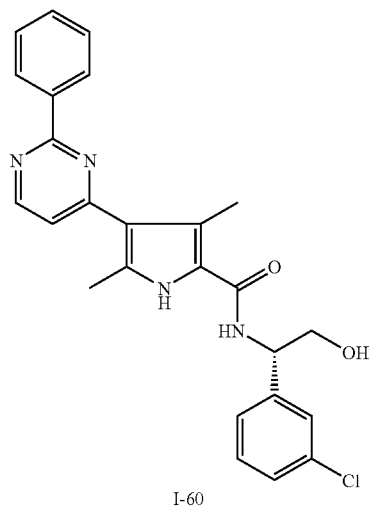
I-60
TABLE 1-continued
Examples of Compounds of Formula I:
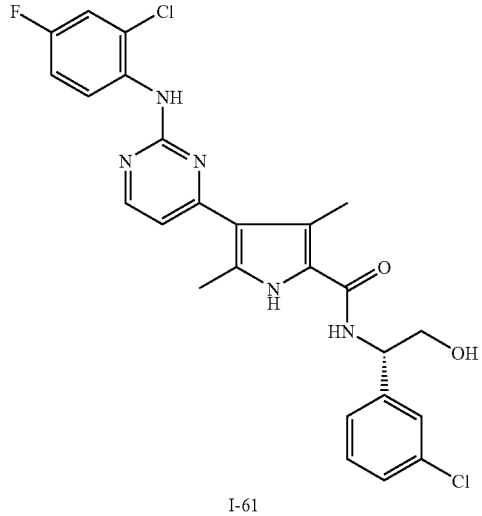
I-61
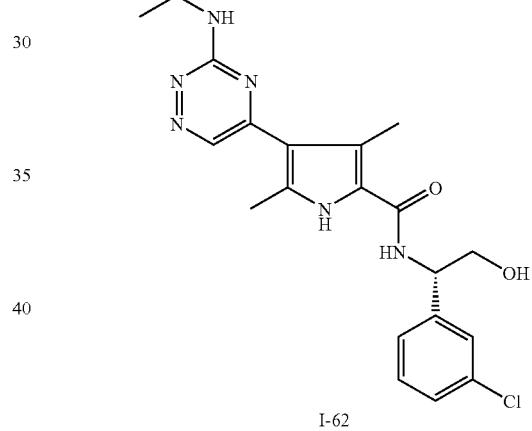
I-62
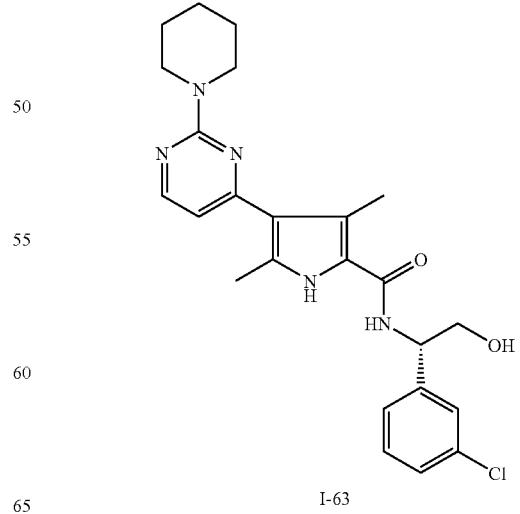
I-63

TABLE 1-continued

Examples of Compounds of Formula I:

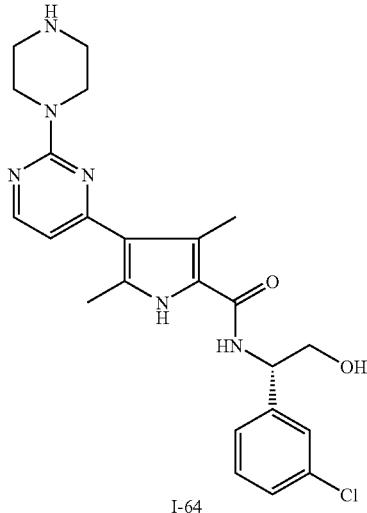
I-64

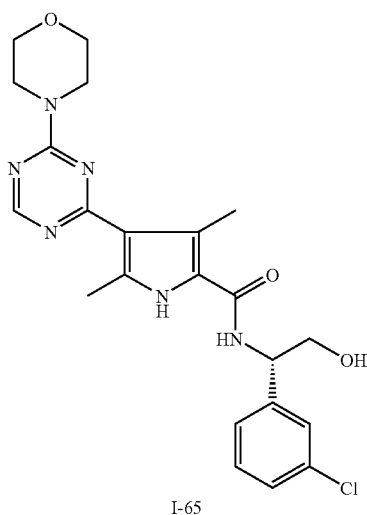
I-65

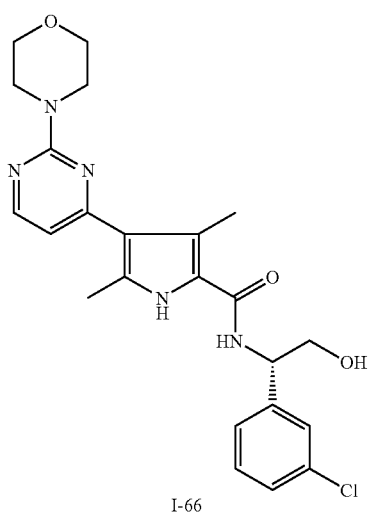
I-66

TABLE 1-continued

Examples of Compounds of Formula I:

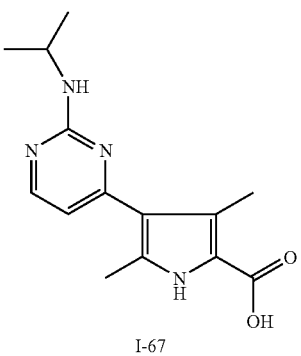
I-67

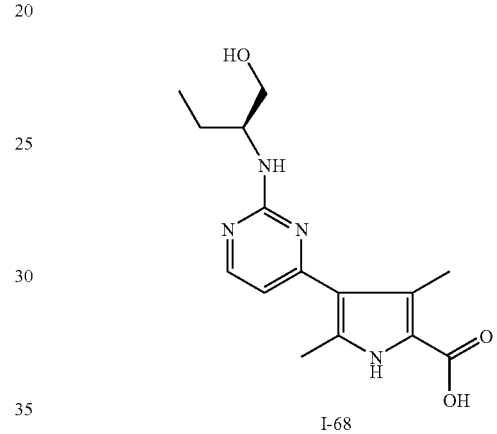
I-68

4. General Methods of Providing the Present Compounds:

The compounds of this invention may be prepared or isolated in general by synthetic and/or pseudo-synthetic methods known to those skilled in the art for analogous compounds and as illustrated by the general Schemes I and II below and the preparative examples that follow.

Scheme I

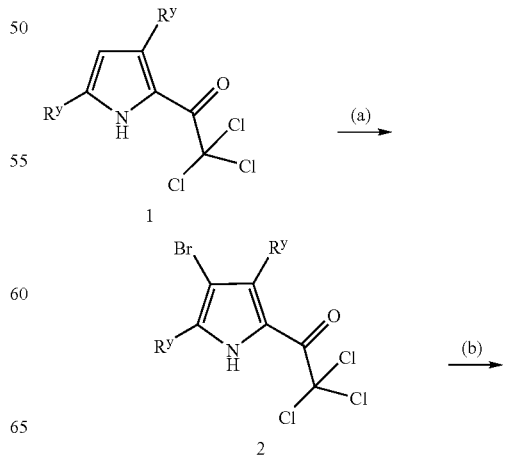

-continued

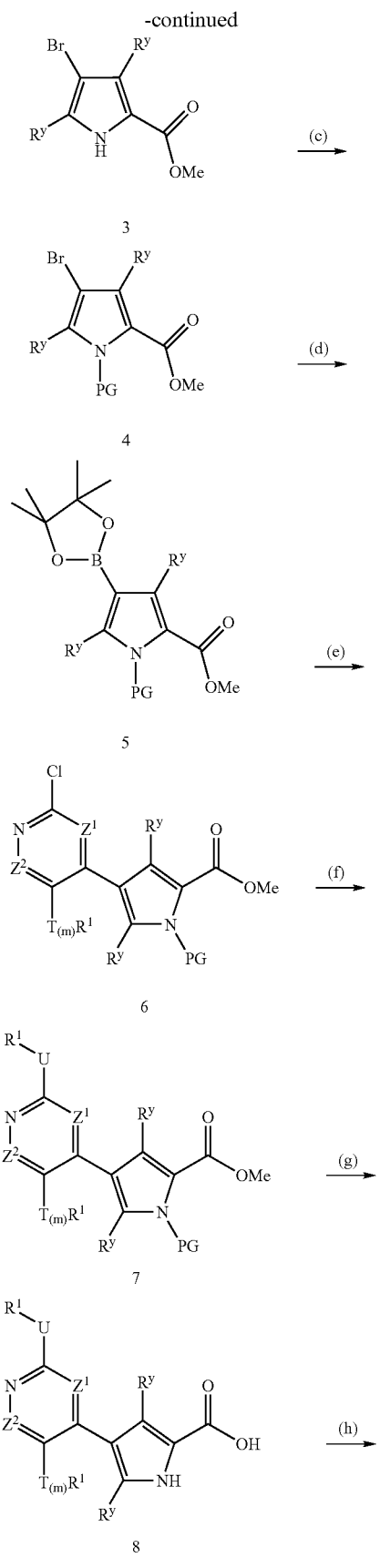

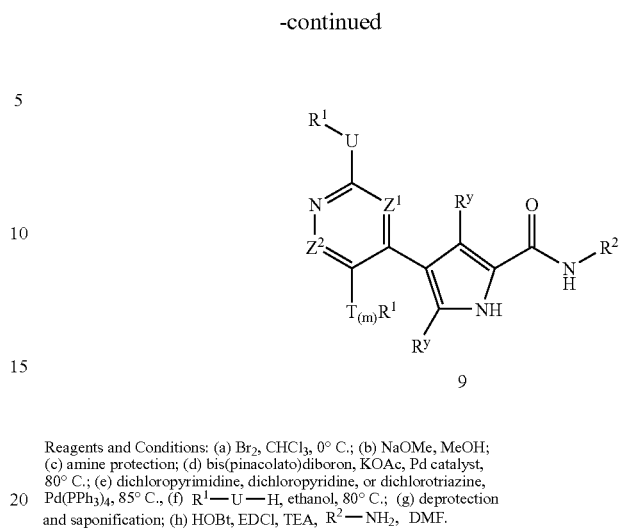

Reagents and Conditions: (a) Br$_2$, CHCl$_3$, 0° C.; (b) NaOMe, MeOH; (c) amine protection; (d) bis(pinacolato)diboron, KOAc, Pd catalyst, 80° C.; (e) dichloropyrimidine, dichloropyridine, or dichlorotriazine, Pd(PPh$_3$)$_4$, 85° C., (f) R$^1$—U—H, ethanol, 80° C.; (g) deprotection and saponification; (h) HOBt, EDCl, TEA, R$^2$—NH$_2$, DMF.

Scheme I above depicts a general method for preparing compounds of formula I wherein Q is —C(O)NH—. At step (a), the pyrrole compound 1 is brominated to form intermediate compound 2. The trichloroacetyl group of compound 2 is treated with methoxide to form the methyl ester compound 3. At step (c), the —NH group of the pyrrole ring is protected with a suitable amino protecting group. One of skill in the art would recognize that a variety of protecting groups are suitable for the above reaction. Amino protecting groups are well known in the art and are described in detail in *Protecting Groups in Organic Synthesis*, Theodora W. Greene and Peter G. M. Wuts, 1991, published by John Wiley and Sons, the entirety of which is hereby incorporated by reference.

The protected pyrrolyl compound 4 is treated with bis(pinacolato)diboron to form compound 5 which is then treated with the appropriate dichloride in the presence of Pd(PPh$_3$)$_4$ to form the pyrrolyl compound 6. The chloro group of compound 6 is readily displaced by a variety of groups, at step (f), to form compounds of the general formula 7. One of ordinary skill in the art would recognize that a wide variety of —U—R$^1$ groups are amenable to displacing the chloro group at step (f) to form compounds 7. Alternatively, one of ordinary skill in the art would recognize that the chloro group of compound 6 is readily displaced by other leaving groups, e.g. I, OTs, OTf, etc., which may, in turn, be displaced by the —U—R$^1$ groups of the present invention. At step (g), the pyrrolyl protecting group is removed and the ester saponified to form compound 8. The carboxyl moiety of compound 8 may then be coupled to a variety of amines to form compounds of the present invention where Q is —C(O)NH—. Alternatively, one of ordinary skill in the art would recognize that a variety of compounds of the present invention are readily obtained from the carboxylic acid compound 8. For example, compound 8 is coupled with a variety of amines to prepare the amide compounds depicted or, alternatively, with a variety of alcohols to prepare compounds of the present invention wherein Q is —C(O)O—.

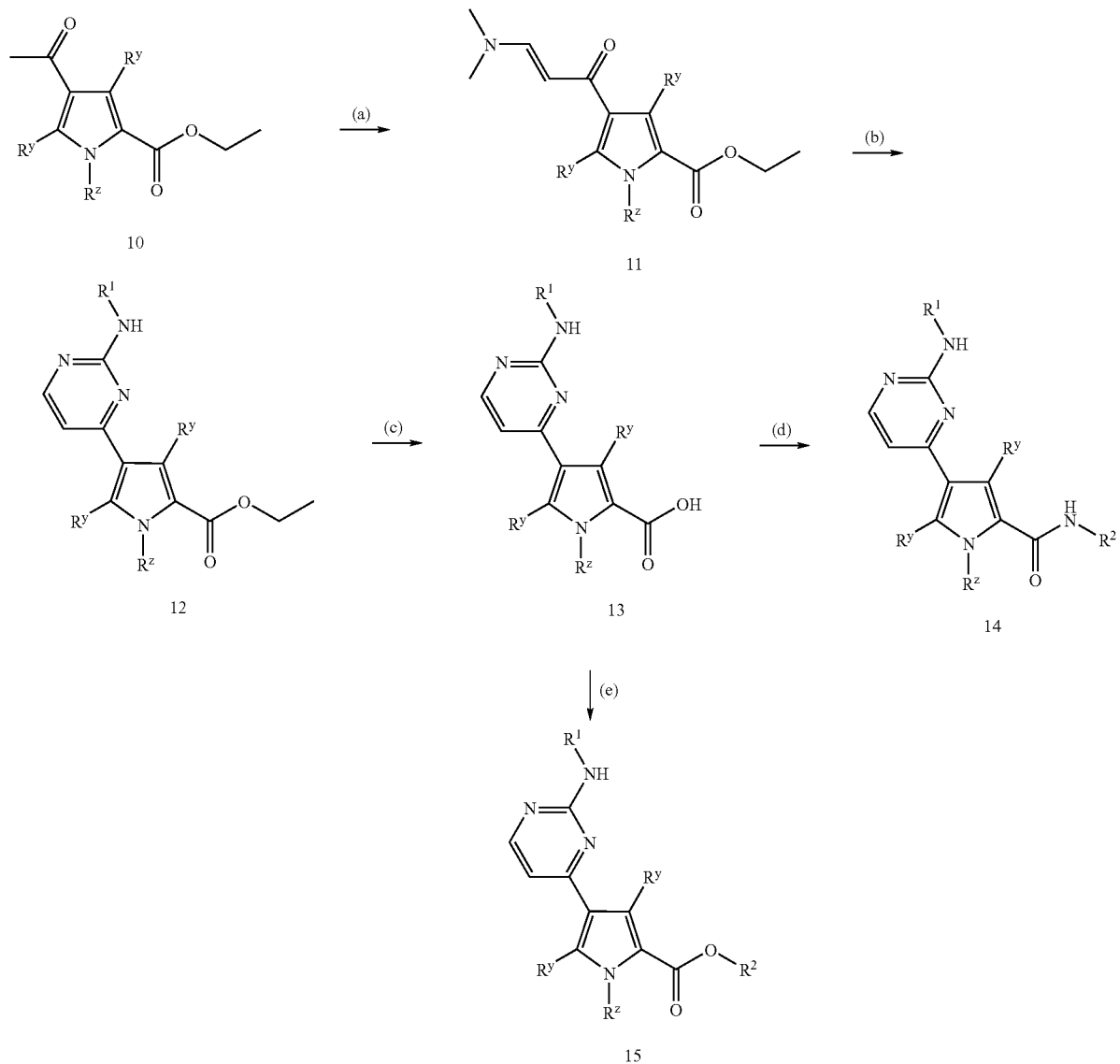

Reagents and Conditions: (a) Brederick's reagent, THF, 50° C.; (b) R¹-guanidine, NaOEt, EtOH, 80° C.; (c) NAOH, MeOH, 80° C.; (d) HOBt, EDCl, TEA, R²—NH₂, DMF. (e) R²—OH, standard coupling conditions.

Scheme II above depicts a general method for preparing certain compounds of the present invention, wherein U is —NH—, $Z^1$ is N, and $Z^2$ is CH. The pyrrole compound 10 is treated with Brederick's reagent to form the enamine compound 11 which is then treated with the desired guanidine derivative to form the pyrimidine compound 12. The ester moiety of compound 12 is saponified and the resulting carboxylate (13) coupled to an amine of formula $R^2$—$NH_2$ to form compound 14. One of ordinary skill in the art would recognize that from carboxylate compound 13, a variety of compounds of the present invention are readily obtained using methods known in the art. For example, the carboxylic acid compound 13 is coupled with a variety of amines to prepare the amide compounds of formula 14 or, alternatively, with a variety of alcohols to prepare compounds of formula 15. One of ordinary skill in the art would also recognize that these coupling reactions may be performed using a variety of conditions known in the art.

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to cancer, autoimmune disorders, neurodegenerative and neurological disorders, schizophrenia, bone-related disorders, liver disease, and cardiac disorders. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of ERK2, JNK3, SRC, Aurora2, or GSK3 protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of cancer, an autoimmune disorder, a neurodegenerative or neurological disorder, schizophrenia, a bone-related disorder, liver disease, or a cardiac disorder is provided comprising administering an effective amount of a compound of the present invention, or a pharmaceutically acceptable composition comprising a compound of the present invention to a subject in need thereof. In certain embodiments of the present invention an "effective amount" of the compound or pharmaceutically acceptable composition is that amount effective for treating or lessening the severity of a disease, condition, or disorder selected from cancer, an autoimmune disorder, a neurodegenerative or neurological disorder, schizophrenia, a bone-related disorder, liver disease, or a cardiac disorder. The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar--agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of ERK2, JNK3, SRC, Aurora2, or GSK3 protein kinases and thus, without wishing to be bound by any particular theory, the compounds and compositions are particularly useful for treating or lessening the severity of a disease, condition, or disorder where activation of one or more of ERK2, JNK3, SRC, Aurora2, or GSK3 protein kinases is implicated in the disease, condition, or disorder. When activation of ERK2, JNK3, SRC, Aurora2, or GSK3 protein kinases is implicated in a particular disease, condition, or disorder, the disease, condition, or disorder may also be referred to as "ERK2-, JNK3-, SRC-, Aurora2-, or GSK3-mediated disease", condition, or disease symptom. Accordingly, in another aspect, the present invention provides a method for treating or lessening the severity of a disease, condition, or disorder where activation or one or more of ERK2, JNK3, SRC, Aurora2, or GSK3 protein kinases is implicated in said disease, condition, or disorder.

The activity of a compound utilized in this invention as an inhibitor of ERK2, JNK3, SRC, Aurora2, or GSK3 protein kinases may be assayed in vitro, in vivo or in a cell line. In vitro assays include assays that determine inhibition of either the phosphorylation activity or ATPase activity of activated ERK2, JNK3, SRC, Aurora2, or GSK3 protein kinases. Alternate in vitro assays quantitate the ability of the inhibitor to bind to ERK2, JNK3, SRC, Aurora2, or GSK3 protein kinases. Inhibitor binding may be measured by radiolabelling the inhibitor prior to binding, isolating the inhibitor/ERK2, inhibitor/JNK3, inhibitor/SRC, inhibitor/Aurora2, or inhibitor/GSK3 complex and determining the amount of radiolabel bound. Alternatively, inhibitor binding may be determined by running a competition experiment where new inhibitors are incubated with ERK2, JNK3, SRC, Aurora2, or GSK3 protein kinases bound to known radioligands.

The term "measurably inhibit", as used herein means a measurable change in ERK2, JNK3, SRC, Aurora2, or GSK3 protein kinase activity between a sample comprising said composition and a ERK2, JNK3, SRC, Aurora2, or GSK3 protein kinase and an equivalent sample comprising ERK2, JNK3, SRC, Aurora2, or GSK3 protein kinase in the absence of said composition. Such measurements of protein kinase activity are known to one of ordinary skill in the art and include those methods set forth herein below.

According to another embodiment, the invention relates to a method of inhibiting ERK2, JNK3, SRC, Aurora2, or GSK3 protein kinase activity in a patient comprising the step of administering to said patient a compound of the present invention, or a composition comprising said compound.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Accordingly, another embodiment of the present invention relates to treating or lessening the severity of one or more diseases in which ERK is known to play a role. Specifically, the present invention relates to a method of treating or lessening the severity of a disease or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein said method comprises administering to a patient in need thereof a composition according to the present invention.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another embodiment relates to a method of treating melanoma, breast cancer, colon cancer, or pancreatic cancer in a patient in need thereof.

The term "Aurora-2-mediated disease" or "Aurora-2-mediated condition", as used herein, means any disease or other deleterious condition in which Aurora is known to play a role. The terms "Aurora-2-mediated disease" or "Aurora-2-mediated condition" also mean those diseases or conditions that are alleviated by treatment with an Aurora-2 inhibitor. Accordingly, another embodiment of the present invention relates to treating or lessening the severity of one or more diseases in which Aurora-2 is known to play a role. Specifically, the present invention relates to a method of treating or lessening the severity of a disease or condition selected from melanoma, lymphoma, neuroblastoma, leukemia, or a cancer selected from colon, breast, lung, kidney, ovary, pancreatic, renal, CNS, cervical, prostate, or cancer of the gastric tract.

The term "GSK3-mediated disease" or "condition", as used herein means any disease or other deleterious condition in which GSK3 is known to play a role. Accordingly, another embodiment of the present invention relates to treating or lessening the severity of one or more diseases in which GSK3 is known to play a role. Specifically, the present invention relates to a method of treating or lessening the severity of a disease or condition selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease wherein said method comprises administering to a patient in need thereof a composition according to the present invention.

According to another embodiment, the present invention relates to a method for treating or lessening the severity of a disease or condition selected from allergy, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), an injury due to head trauma, schizophrenia, anxiety, bipolar disorder, tauopothy, a spinal cord or peripheral nerve injury, myocardial infarction, cardiomyocyte hypertrophy, glaucoma, attention deficit disorder (ADD), depression, a sleep disorder, reperfusion/ischemia, stroke, an angiogenic disorder, or baldness, wherein said method comprises administering to a patient in need thereof a compound of the present invention or composition thereof.

According to one embodiment, the method of the present invention relates to treating or lessening the severity of stroke, wherein said method comprises administering to a patient in need thereof a compound of the present invention or composition thereof.

According to another embodiment, the method of the present invention relates to treating or lessening the severity of a neurodegenerative or neurological disorder, wherein said method comprises administering to a patient in need thereof a compound of the present invention or composition thereof.

Yet another embodiment of the present invention relates to a method of treating depression, wherein said method comprises administering to a patient in need thereof a compound of the present invention or composition thereof.

Another aspect of the present invention relates to a method of decreasing sperm motility in a male patient comprising administering to said patient a compound of the present invention or composition thereof.

The term "JNK-mediated condition", as used herein means any disease or other deleterious condition in which JNK is known to play a role. Accordingly, another embodiment of the present invention relates to treating or lessening the severity of one or more diseases in which JNK is known to play a role. Specifically, the present invention relates to a method of treating or lessening the severity of a disease or condition selected from inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

"JNK-mediated conditions" also include ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T-cell activation and thrombin-induced platelet aggregation.

In addition, JNK compounds of the instant invention may inhibit the expression of inducible pro-inflammatory proteins. Therefore, other "JNK-mediated conditions" which can be treated by the compounds of this invention include edema, analgesia, fever and pain, such as neuromuscular pain, headache, cancer pain, dental pain and arthritis pain.

The terms "Src-mediated disease" or "Src-mediated condition", as used herein mean any disease or other deleterious condition in which Src is known to play a role. The terms "Src-mediated disease" or "Src-mediated condition" also mean those diseases or conditions that are alleviated by treatment with a Src inhibitor. Accordingly, another embodiment of the present invention relates to treating or lessening the severity of one or more diseases in which Src is known to play a role. Specifically, the present invention relates to a method of treating or lessening the severity of a disease or condition selected from hypercalcemia, osteoporosis, osteoarthritis, cancer, symptomatic treatment of bone metastasis, and Paget's disease.

In other embodiments, the invention relates to a method of enhancing glycogen synthesis and/or lowering blood levels of glucose in a patient in need thereof, comprising administering to said patient a therapeutically effective amount of a composition comprising a compound of the present invention. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of the present invention. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of the present invention. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting JNK3, SRC, Aurora2, or GSK3 protein kinase activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of JNK3, SRC, Aurora2, or GSK3 protein kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

As used herein, the term "$R_t$(min)" refers to the HPLC retention time, in minutes, associated with the compound. Unless otherwise indicated, the HPLC method utilized to obtain the reported retention time is as follows:

Column: YMC ODS—AQ, 5 micron silica, 3×100 mm
Gradient: 10-90% acetonitrile in water w/0.1% TFA
Flow rate: 1.5 mL/minute Unless otherwise indicated, each $^1$H NMR was obtained at 500 MHz in CDCl$_3$ and compound numbers correspond to those compound numbers recited in Table 1.

Example 1

4-(3-Dimethylamino-acryloyl)-3,5-dimethyl-1H-pyrrole-2-carboxylic acid ethyl ester In a dry flask containing THF (15 mL) was added 4-acetyl-3,5-dimethyl-1H-pyrrole-2-carboxylic acid ethyl ester (2.0 g, 9.3 mmol) then Bredereck's reagent (5 mL). The reaction was stirred at 50° C. for 20 hours. The resulting precipitate formed during the reaction was removed by filtration and washed with hexanes. The enaminone was recovered as a yellow solid (2.2 g), HPLC $R_t$=4.0 minutes; FIA, ES+=265.1

Example 2

4-(2-Isopropylamino-pyrimidin-4-yl)-3,5-dimethyl-1H-pyrrole-2-carboxylic acid ethyl ester (I-48): In a dry flask containing ethanol(10 mL, absolute) was added 4-(3-dimethylamino-acryloyl)-3,5-dimethyl-1H-pyrrole-2-carboxylic acid ethyl ester (509 mg, 1.93 mmol), isopropyl guanidine hydrochloride (1.5 eq., 292 mg, 2.9 mmol) and sodium ethoxide (3 eq., 515 mg, 5.8 mmol). The reaction mixture was heated at 80° C. for 24 hours then cool down to ambient temperature and filtered through Celite® with methanol washes. The crude product was purified by preparative HPLC (actetonitrile/water) to afford the title compound (32 mg) as a solid. HPLC $R_t$=4.98 minutes; FIA, ES+=303.2.

Example 3

4-(2-Isopropylamino-pyrimidin-4-yl)-3,5-dimethyl-1H-pyrrole-2-carboxylic acid (I-67): In a small flask containing methanol (1 mL) was added 4-(2-isopropylamino-pyrimidin-4-yl)-3,5-dimethyl-1H-pyrrole-2-carboxylic acid ethyl ester (20 mg, 66 µmol) then sodium hydroxide (1N, 0.3 mL)). The reaction mixture was heated at 80° C. for 5 hours. The pH was adjusted to ~2 with hydrochloric acid (1N) and the solvent was evaporated to dryness to afford the title compound. HPLC, $R_t$=3.8 minutes; FIA, ES+=275.1, ES−=273.2.

Example 4

4-(2-Isopropylamino-pyrimidin-4-yl)-3,5-dimethyl-1H-pyrrole-2-carboxylic acid [1-(S)-(3-chlorophenyl)-2-hydroxyethyl]-amide (I-49): In a small flask containing DMF (anydrous, 1 mL) was added 4-(2-isopropylamino-pyrimidin-4-yl)-3,5-dimethyl-1H-pyrrole-2-carboxylic acid (66 µmol), hydroxybenzotriazole hydrate (1.1 eq., 10 mg, 73 µmol), diisopropylethylamine (3 eq., 35 µL, 0.2 mmol) and EDCI (1.3 eq., 17 mg, 86 µmol). The reaction mixture was stirred for 15 minutes. To this solution was added 2-amino-2-(S)-(3-chlorophenyl) ethanol hydrochloride (1.2 eq., 17 mg, 79 µmol). After 8 hours of stirring at ambient temperature, the crude product was purified by preparative HPLC (acetonitrile/water) to afford the title compound as a solid (7.5 mg). HPLC $R_t$=4.99 minutes; FIA, ES+=428.1, ES−=426.6. $^1$H NMR (MeOH-d4): 8.05 (d, 1H), 7.4 (s, 1H), 7.2-7.3 (m, 3H), 7.05 (d, 1H), 5.1 (m, 1H), 3.85 (m, 2H), 2.55 (2×s, 6H),1.3 (2×s, 6H).

Example 5

4-[2-(S)-(1-Hydroxymethyl-propylamino)-pyrimidin4-yl]-3,5-dimethyl-1H-pyrrole-2-carboxylic acid ethyl ester (I-50): The title compound was prepared by methods substantially similar to that described for Example 2.

Example 6

4-[2-(S)-(1-Hydroxymethyl-propylamino)-pyrimidin-4-yl]-3,5-dimethyl-1H-pyrrole-2-carboxylic acid (I-68):

The title compound was prepared by methods substantially similar to that described for Example 3.

Example 7

4-[2-(S)-(1-Hydroxymethyl-propylamino)-pyrimidin-4-yl]-3,5-dimethyl-1H-pyrrole-2-carboxylic acid [1-(S)-(3-chloro-phenyl)-2-hydroxyethyl]-amide (I-51): The title compound was prepared by methods substantially similar to that described for Example 4. M−=456.5; M+=458; $^1$H NMR (MeOH-d4): 8.05 (d, 1H), 7.0-745 (4×m, 5H), 5.15 (m, 1H), 3.55-4.3 (m, 5H), 2.6 (2×s, 6H), 1.5-1.8 (2×m, 2H),1.0 (t, 3H).

Example 8

Other compounds of the present invention were prepared by methods substantially similar to those described in the above Examples 1-7, those illustrated in Schemes I and II, and those known in the art. The characterization data for these compounds is summarized in Table 2 below and includes MS, HPLC retention time, and $^1$H NMR data. Compound numbers in Table 2 correspond to the compound numbers listed in Table 1.

TABLE 2

Characterization Data for Selected Compounds of Formula I

| Compound No | M + 1 (obs) | M − 1 (obs) | $R_t$ | $^1$H NMR |
|---|---|---|---|---|
| I-14 | 365.5 | 363.2 | 3.73 | — |
| I-15 | 444.2 | 442.2 | 3.42 | — |
| I-16 | 400.2 | 398.2 | 3.86 | — |
| I-17 | 399.2 | 397.2 | 4.14 | — |
| I-18 | 395.3 | — | 3.77 | — |
| I-19 | 471.2 | 469.3 | 4.36 | — |
| I-20 | 298.0 | — | 2.98 | — |
| I-21 | 303.0 | — | 3.22 | — |
| I-22 | 317.0 | — | 3.41 | — |
| I-24 | 343.3 | — | 3.93 | — |

TABLE 2-continued

Characterization Data for Selected Compounds of Formula I

| Compound No | M + 1 (obs) | M − 1 (obs) | $R_t$ | $^1$H NMR |
|---|---|---|---|---|
| I-60 | 447 | 445.3 | — | (MeOH-d4): 8.7 (d, 1H), 8.4 (m, 2H), 7.8 (m, 1H), 7.3-7.5 (4x m, 7H), 5.15 (m, 1H), 3.85 (m, 2H), 2.6 (2x s, 6H). |
| I-61 | 445.2 | 443 | — | (MeOH-d4): 8.2 (d, 1H), 7.75 (m, 1H), 7.1-7.4 (m,, 7H), 5.1 (m, 1H), 3.8 (m, 2H), 2.45 (s, 3H), 2.35 (s, 3H)., NMR 1H |

Example 9

Aurora-2 Inhibition Assay:

Compounds were screened in the following manner for their ability to inhibit Aurora-2 using a standard coupled enzyme assay (Fox et al., *Protein Sci.* 1998, 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (American Peptide, Sunnyvale, Calif.) was added a DMSO solution of a compound of the present invention to a final concentration of 30 μM. The resulting mixture was incubated at 30° C. for 10 minutes. The reaction was initiated by the addition of 10 μl of Aurora-2 stock solution to give a final concentration of 70 nM in the assay. The rates of reaction were obtained by monitoring absorbance at 340 nm over a 5 minute read time at 30° C. using a BioRad Ultramark plate reader (Hercules, Calif.). The $K_i$ values were determined from the rate data as a function of inhibitor concentration.

Compounds of the present invention were found to be inhibitors of Aurora2 protein kinase. In certain embodiments, compounds were found to inhibit Aurora2 kinase at <5 μM. In other embodiments, compounds were found to inhibit Aurora2 kinase at <1 μM.

Example 10

GSK-3 Inhibition Assay:

Compounds of the present invention were screened for their ability to inhibit GSK-3β (AA 1-420) activity using a standard coupled enzyme system (Fox et al., *Protein Sci.* 1998, 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of the present invention. The assay stock buffer solution (175 μl) was incubated in a 96 well plate with 5 μl of the test compound of the present invention at final concentrations spanning 0.002 μM to 30 μM at 30° C. for 10 minutes. Typically, a 12 point titration was conducted by preparing serial dilutions (from 10 mM compound stocks) with DMSO of the test compounds of the present invention in daughter plates. The reaction was initiated by the addition of 20 μl of ATP (final concentration 20 μM). Rates of reaction were obtained using a Molecular Devices Spectramax plate reader (Sunnyvale, Calif.) over 10 minutes at 30° C. The $K_i$ values were determined from the rate data as a function of inhibitor concentration.

Compounds of the present invention were found to be inhibitors of GSK3 protein kinase. In certain embodiments, compounds were found to inhibit GSK3 kinase at <5 μM. In other embodiments, compounds were found to inhibit GSK3 kinase at <1 μM.

Example 11

JNK3 Inhibition Assays

Compounds were assayed for the inhibition of JNK3 by a spectrophotometric coupled-enzyme assay. In this assay, a fixed concentration of activated JNK3 (10 nM) was incubated with various concentrations of a compound of the present invention dissolved in DMSO for 10 minutes at 30° C. in a solution containing 0.1 M HEPES buffer (pH 7.5), 10 mM $MgCl_2$, 2.5 mM phosphoenolpyruvate, 200 μM NADH, 150 μg/ml pyruvate kinase, 50 μg/ml lactate dehydrogenase, and 200 μM EGF receptor peptide. The EGF receptor is a phosphoryl acceptor in the JNK3-catalyzed kinase reaction. The reaction was initiated by the addition of 10 μM ATP and the assay plate was inserted into the spectrophotometer's assay plate compartment that was maintained at 30° C. The decrease of absorbance at 340 nm was monitored as a function of time. The rate data as a function of inhibitor concentration was fitted to a competitive inhibition kinetic model to determine the $K_i$.

Certain compounds of the present invention have $K_i$ values less than 5.0 micromolar (μM) in the JNK3 inhibition assay. In certain preferred embodiments, the following compounds have $K_i$ values of 1.0 μM or less in the JNK3 inhibition assay:

Compounds of the present invention were found to be inhibitors of JNK3 protein kinase. In certain embodiments, compounds were found to inhibit JNK3 kinase at <5 μM. In other embodiments, compounds were found to inhibit JNK3 kinase at <1 μM.

Example 12

SRC Inhibition Assay:

The compounds of the present invention were evaluated as inhibitors of human Src kinase using either a radioactivity-based assay or spectrophotometric assay.

Src Inhibition Assay A: Radioactivity-Based Assay

The compounds of the present invention were assayed as inhibitors of full length recombinant human Src kinase (from Upstate Biotechnology, Cat. No. 14-117) expressed and purified from baculo viral cells. Src kinase activity was monitored by following the incorporation of $^{33}$P from ATP into the tyrosine of a random poly Glu-Tyr polymer substrate of composition, Glu:Tyr=4:1 (Sigma, Cat. No. P-0275). The final concentrations of the assay components were: 0.05 M HEPES (pH 7.6), 10 mM $MgCl_2$, 2 mM DTT, 0.25 mg/ml BSA, 10 μM ATP (1-2 Ci $^{33}$P-ATP per reaction), 5 mg/ml poly Glu-Tyr, and 1-2 units of recombinant human Src kinase. In a typical assay, all the reaction components with the exception of ATP were pre-mixed and aliquoted into assay plate wells. Compounds of the present invention were dissolved in DMSO and added to the wells to give a final DMSO concentration of 2.5%. The assay plate was incubated at 30° C. for 10 minutes before initiating the reaction with $^{33}$P-ATP. After 20 minutes of reaction, the reactions were quenched with 150 μl of 10% trichloroacetic acid (TCA) containing 20 mM $Na_3PO_4$. The quenched samples were then transferred to a 96-well filter plate (Whatman, UNI-Filter GF/F Glass Fiber Filter, Cat No. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter. The radioactivity incorporated was plotted as a function of the compound of the present invention concentration. The data was fitted to a competitive inhibition kinetics model to give the $K_i$ values for the compounds of the present invention.

Src Inhibition Assay B: Spectrophotometric Assay

The ADP produced from ATP by the human recombinant Src kinase-catalyzed phosphorylation of poly Glu-Tyr substrate was quantified using a coupled enzyme assay (Fox et al., Protein Sci. 1998, 7, 2249). In this assay one molecule of NADH was oxidised to AND for every molecule of ADP produced in the kinase reaction. The disappearance of NADH was conveniently followed at 340 nm.

The final concentrations of the assay components were: 0.025 M HEPES (pH 7.6), 10 mM $MgCl_2$, 2 mM DTT, 0.25 mg/ml poly Glu-Tyr, and 25 nM of recombinant human Src kinase. Final concentrations of the components of the coupled enzyme system were 2.5 mM phosphoenolpyruvate, 200 μM NADH, 30 μg/ml pyruvate kinase and 10 μg/ml lactate dehydrogenase.

In a typical assay, all the reaction components with the exception of ATP were pre-mixed and aliquoted into assay plate wells. Compounds of the present invention dissolved in DMSO were added to the wells to give a final DMSO concentration of 2.5%. The assay plate was incubated at 30° C. for 10 minutes before initiating the reaction with 100 μM ATP. The absorbance change at 340 nm over time was monitored on a molecular devices plate reader. The data was fitted to a competitive inhibition kinetics model to get the $K_i$ values for the compounds of the present invention.

Compounds of the present invention were found to be inhibitors of Src protein kinase. In certain embodiments, compounds were found to inhibit Src kinase at <5 μM. In other embodiments, compounds were found to inhibit Src kinase at <1 μM.

Example 13

ERK2 Inhibition Assay:

Compounds were assayed for the inhibition of ERK2 by a spectrophotometric coupled-enzyme assay (Fox et al (1998) Protein Sci 7, 2249). In this assay, a fixed concentration of activated ERK2 (10 nM) was incubated with various concentrations of the compound in DMSO (2.5%) for 10 minutes at 30° C. in 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The $IC_{50}$ was evaluated from the rate data as a function of inhibitor concentration.

Compounds of the present invention we found to be inhibitors of ERK2 protein kinase. In certain embodiments, compounds were found to inhibit ERK2 kinase at <5 μM. In other embodiments, compounds were found to inhibit ERK2 kinase at <1 μM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I:

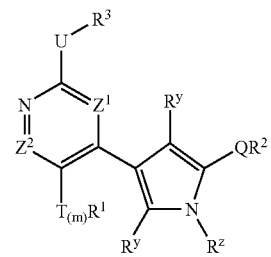

or a pharmaceutically acceptable salt thereof, wherein:
  $R^z$ is hydrogen R;
  each $R^y$ is an optionally substituted $C_{1-4}$ aliphatic group
  $Z^1$ is N;
  $Z^2$ is CH;
  $T_{(m)}R^1$ is hydrogen;
  U is NH;
  Q is —C(O)N(R)— or —C(O)O—;
  $R^2$ is selected from $(CH_2)_y R^5$, $(CH_2)_y CH(R^5)_2$, or $(CH_2)_y CH(R^7)CH(R^5)_2$;
  y is 0-6;
  each Ar is independently selected from an optionally substituted 3-7 membered saturated, partially unsaturated, or fully unsaturated monocyclic ring having 0-4 heteroatoms independently selected from nitrogen, oxygen, or sulfur, or an optionally substituted 8-10 membered saturated, partially unsaturated, or fully unsaturated bicyclic ring having 0-4 heteroatoms independently selected from nitrogen, oxygen, or sulfur;
  $R^3$ is selected from hydrogen, $CH(R^7)R^5$, a 3-7 membered carbocyclyl, or an optionally substituted group selected from $C_{1-4}$ aliphatic, a 3-6 membered heterocyclic ring having 1-3 heteroatoms independently selected from nitrogen, oxygen, or sulfur, or a 5-6 membered aryl or heteroaryl ring having 1-3 heteroatoms independently selected from nitrogen, oxygen, or sulfur;
  each R is independently selected from hydrogen or an optionally substituted $C_{1-6}$ aliphatic group, or:
  two R on the same nitrogen atom are taken together with the nitrogen atom attached thereto to form a 4-8 membered saturated, partially unsaturated, or fully unsaturated ring having 1-4 heteroatoms independently selected from nitrogen, oxygen, or sulfur;
  each $R^4$ is independently selected from $R^6$, $C(O)R^6$, $CO_2R^6$, $CON(R^6)_2$, $SO_2R^6$;

each $R^5$ is independently selected from $R^6$, $OR^6$, $CO_2R^6$, $(CH_2)_yN(R^4)_2$, $N(R^4)_2$, $N(R)C(O)R^6$, $N(R)CON(R^6)_2$, $CON(R^6)_2$, $SO_2R^6$, $N(R)SO_2R^6$, $C(O)R^6$, $CN$, or $SO_2N(R^6)_2$;

each $R^6$ is independently selected from R or Ar;

$R^7$ is selected from $R^6$, $(CH_2)_wOR^6$, $(CH_2)_wN(R^4)_2$, or $(CH_2)_wSR^6$; and each w is independently selected from 0-4.

2. The compound according to claim 1, wherein $R^3$ is $CH(R^7)R^5$.

3. The compound according to claim 1, wherein $R^3$ is a 3-6 membered heterocyclic ring having 1-3 heteroatoms independently selected from nitrogen, oxygen, or sulfur.

4. The compound according to claim 1, wherein said compound has the formula III:

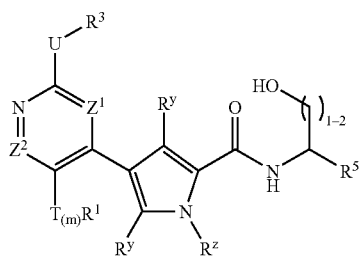

III or a pharmaceutically acceptable salt thereof.

5. The compound according to claim 1, wherein said compound has the formula IV:

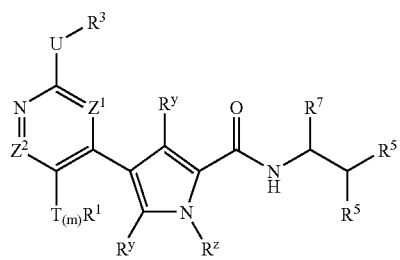

IV or a pharmaceutically acceptable salt thereof.

6. The compound according to claim 1, wherein said compound is selected from the group consisting of:

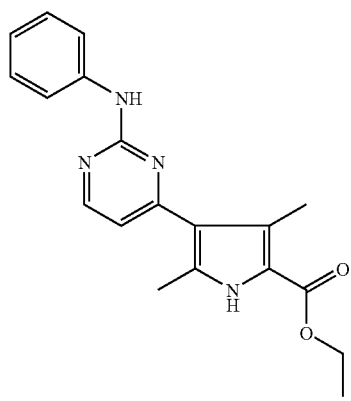

I-1

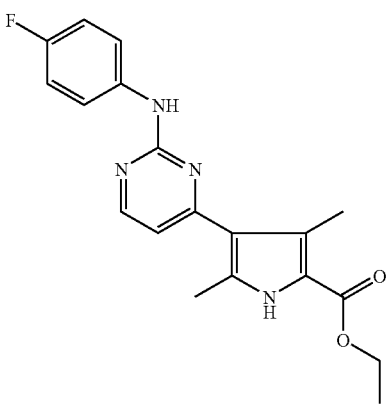

I-2

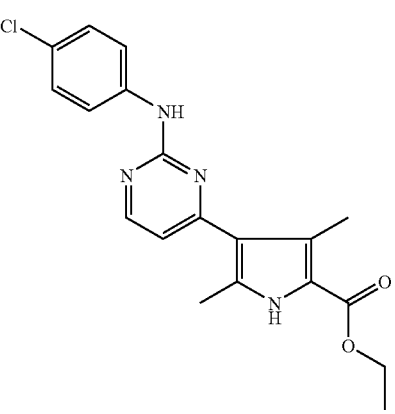

I-3

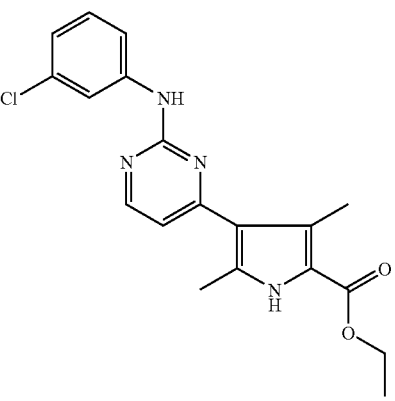

I-4

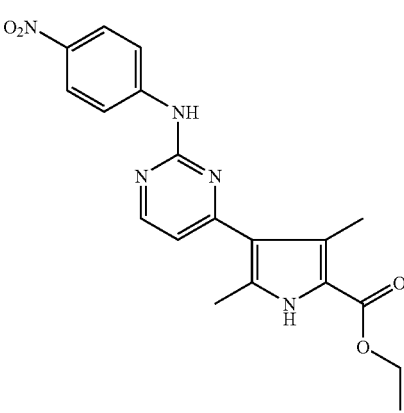

I-5

-continued
I-6
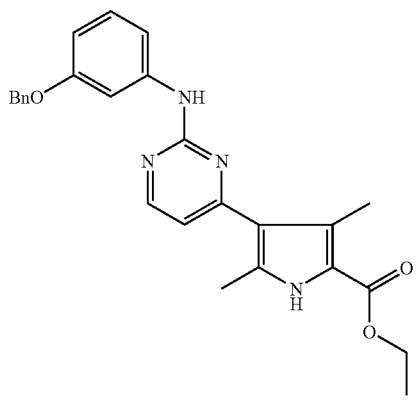
I-7
I-14
I-15
-continued
I-16
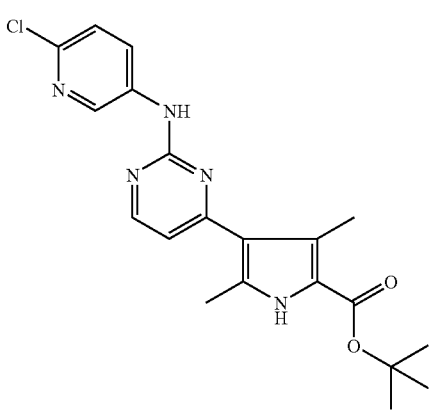
I-17
I-18
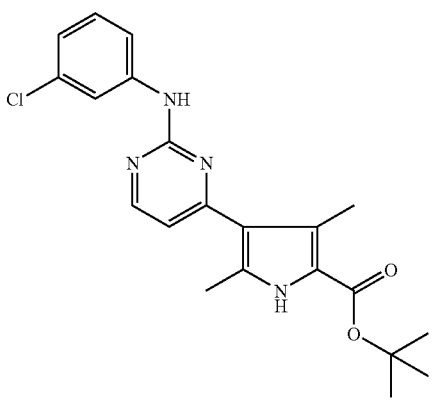
I-19
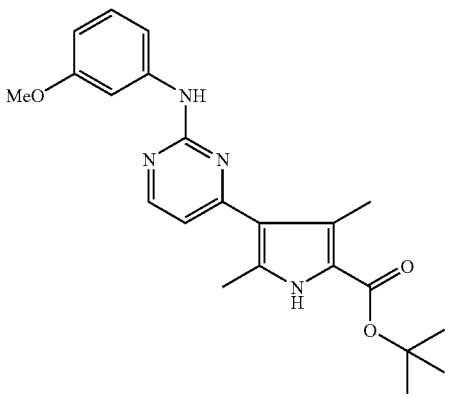
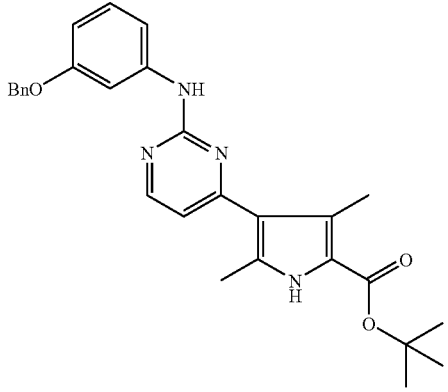

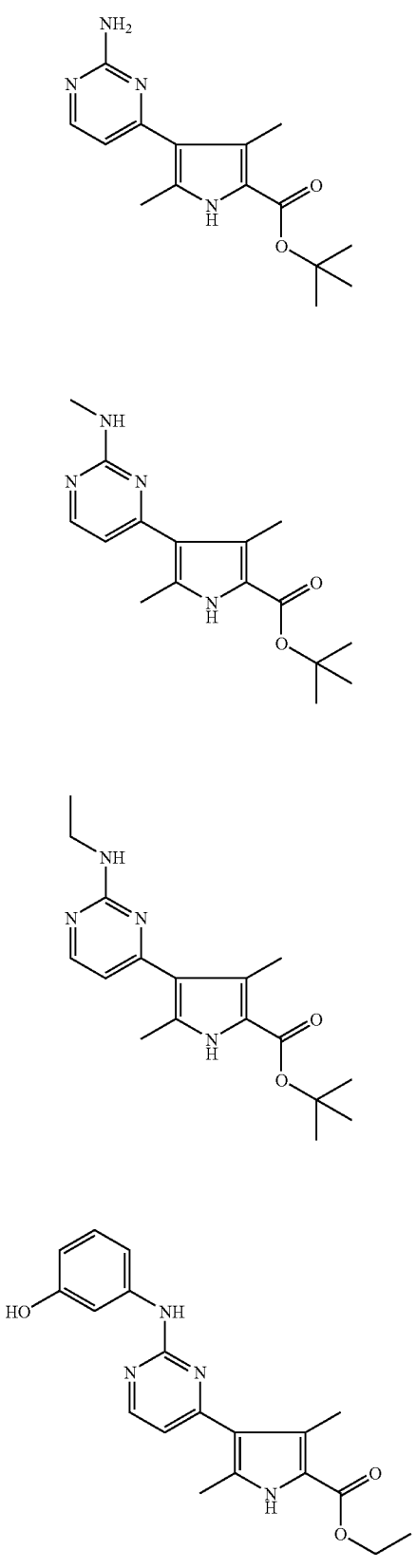

-continued
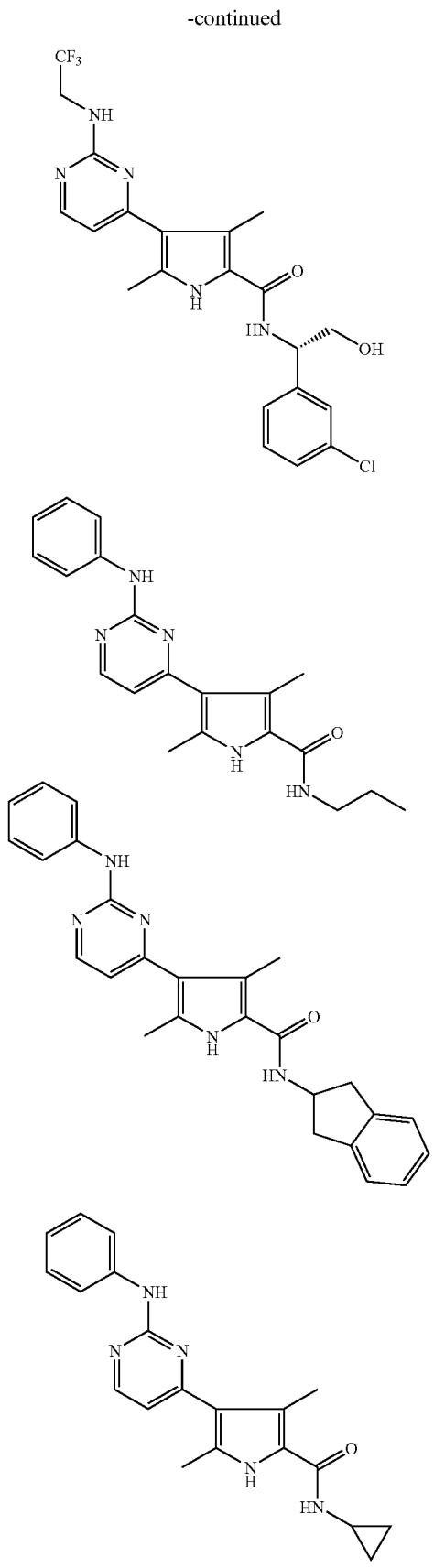
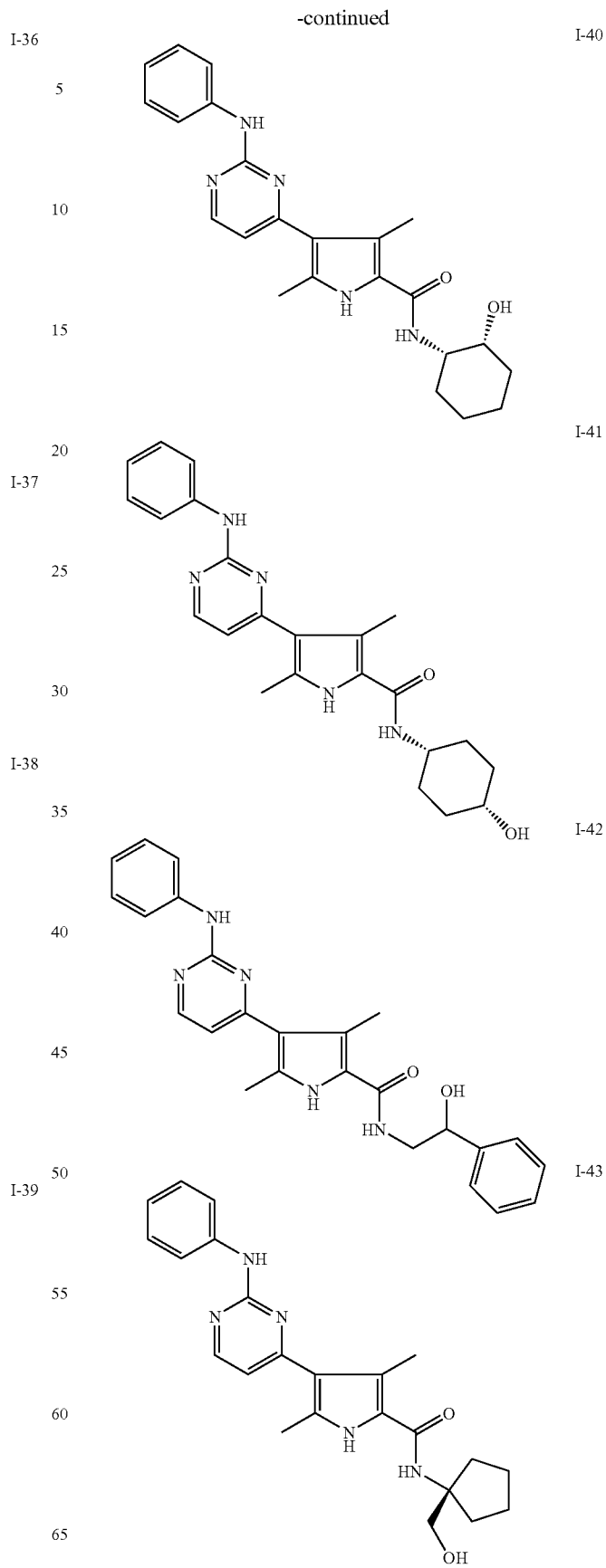

-continued
I-44
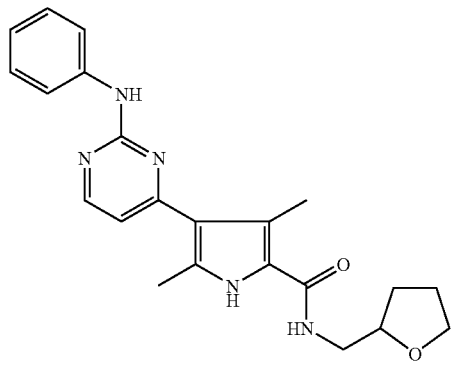
I-45
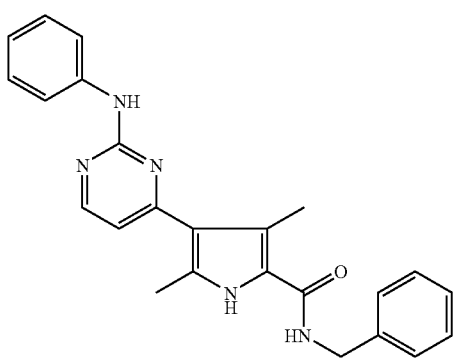
I-48
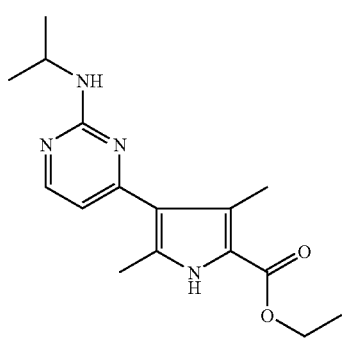
I-49
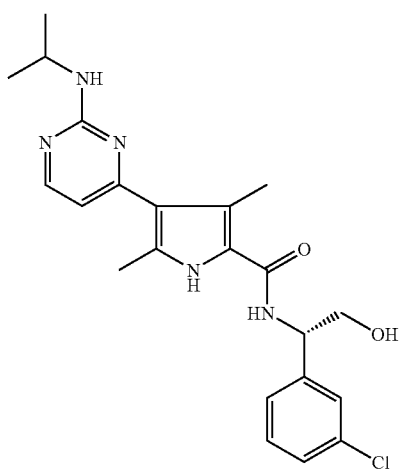
-continued
I-50
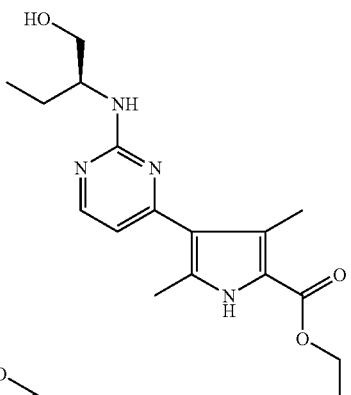
I-51
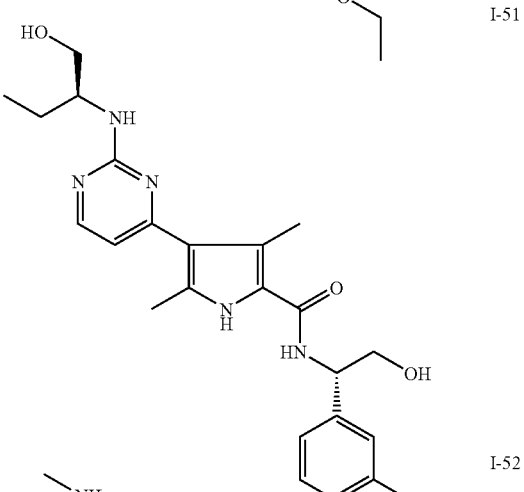
I-52
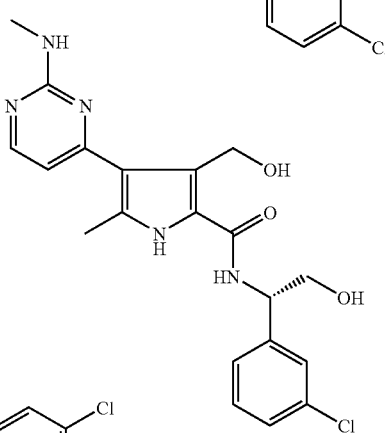
I-61
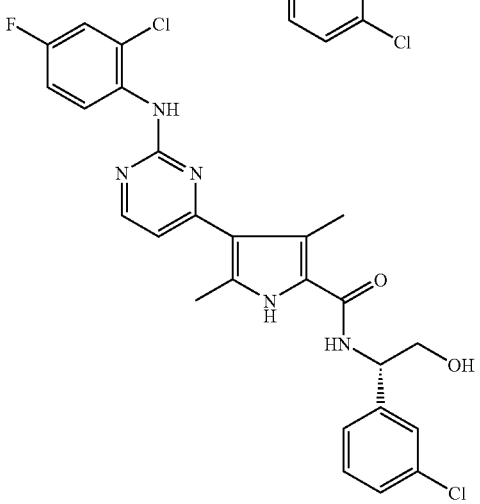

I-67

I-68

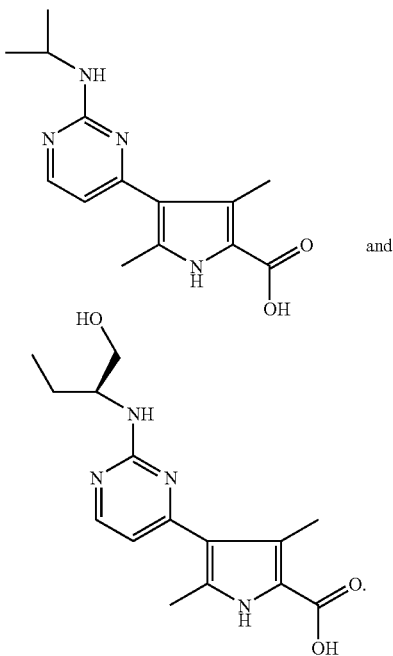
and

7. A composition comprising an effective amount of a compound according to claim 1, and a pharmaceutically acceptable carrier, adjuvant, or vehicle.

8. The composition of claim 7, additionally comprising a therapeutic agent selected from a chemotherapeutic or antiproliferative agent selected from mechlorethamine, chlorambucil, cyclophosphamide, melphalan, ifosfamide, methotrexate, 6-mercaptopurine, 5-fluorouracil, cytarabile, gemcitabine, vinblastine, vincristine, vinorelbine, paclitaxel, etoposide, irinotecan, topotecan, doxorubicin, bleomycin, mitomycin, carmustine, lomustine, cisplatin, carboplatin, asparaginase, tamoxifen, leuprolide, flutamide, megestrol, imatinib, adriamycin, dexamethasone, or cyclophosphamide.

9. A method of inhibiting ERK2, JNK3, SRC, Aurora2, or GSK3 protein kinase activity in a biological sample selected from a cell culture, saliva, urine, feces, semen, tears, or an extract thereof, which method comprises contacting said biological sample in vitro with:

a) a composition according to claim 7; or b) a compound according to claim 1.

* * * * *